US011162097B2

(12) United States Patent
Monteleone

(10) Patent No.: US 11,162,097 B2
(45) Date of Patent: Nov. 2, 2021

(54) METHODS OF TREATING INTESTINAL FIBROSIS USING SMAD7 INHIBITION

(71) Applicant: Nogra Pharma Limited, Dublin (IE)

(72) Inventor: Giovanni Monteleone, Grottaferrata (IT)

(73) Assignee: Nogra Pharma Limited, Dublin (IE)

( * ) Notice: Subject to any disclaimer, the term of this patent is extended or adjusted under 35 U.S.C. 154(b) by 0 days.

(21) Appl. No.: 16/079,059

(22) PCT Filed: Feb. 23, 2017

(86) PCT No.: PCT/US2017/019094
§ 371 (c)(1),
(2) Date: Aug. 22, 2018

(87) PCT Pub. No.: WO2017/147276
PCT Pub. Date: Aug. 31, 2017

(65) Prior Publication Data
US 2019/0055559 A1 Feb. 21, 2019

Related U.S. Application Data

(60) Provisional application No. 62/298,988, filed on Feb. 23, 2016.

(51) Int. Cl.
*C12N 15/113* (2010.01)
*A61K 31/7088* (2006.01)
*G01N 33/68* (2006.01)
*C12Q 1/6883* (2018.01)
*C07K 14/495* (2006.01)

(52) U.S. Cl.
CPC ........ *C12N 15/113* (2013.01); *A61K 31/7088* (2013.01); *C12Q 1/6883* (2013.01); *G01N 33/6863* (2013.01); *C07K 14/495* (2013.01); *C12N 2310/11* (2013.01); *C12N 2310/315* (2013.01); *C12N 2310/334* (2013.01); *C12N 2320/35* (2013.01); *C12Q 2600/106* (2013.01); *C12Q 2600/158* (2013.01); *G01N 2333/4712* (2013.01); *G01N 2333/495* (2013.01); *G01N 2800/06* (2013.01); *G01N 2800/52* (2013.01)

(58) Field of Classification Search
CPC .............. C12N 15/113; C12N 2310/11; C12N 2310/315; C12Q 1/6883; G01N 33/6863; G01N 2800/06
See application file for complete search history.

(56) References Cited

U.S. PATENT DOCUMENTS

| 7,700,572 B2 | 4/2010 | Steinbrecher et al. |
| 7,700,757 B2 | 4/2010 | Monteleone et al. |
| 7,807,818 B2 | 10/2010 | Monteleone et al. |
| 8,106,182 B2 | 1/2012 | Monteleone et al. |
| 8,648,186 B2 * | 2/2014 | Monteleone ......... C12N 15/113 536/24.5 |
| 8,907,078 B2 | 12/2014 | Monteleone et al. |
| 8,912,154 B2 | 12/2014 | Baroni et al. |
| 9,006,418 B2 | 4/2015 | Monteleone et al. |
| 9,096,854 B1 | 8/2015 | Monteleone et al. |
| 9,279,126 B2 | 3/2016 | Monteleone et al. |
| 9,314,434 B2 | 4/2016 | Baroni et al. |
| 9,382,541 B2 | 7/2016 | Monteleone et al. |
| 9,499,819 B2 | 11/2016 | Wang et al. |
| 9,518,264 B2 | 12/2016 | Monteleone et al. |
| 9,605,264 B2 | 3/2017 | Monteleone et al. |
| 9,682,923 B2 * | 6/2017 | Baroni ................. A61K 31/196 |
| 9,791,442 B2 | 10/2017 | Monteleone et al. |
| 9,951,334 B2 | 4/2018 | Monteleone et al. |
| 9,982,264 B2 | 5/2018 | Baroni et al. |
| 10,006,029 B2 | 6/2018 | Monteleone et al. |
| 10,036,022 B2 | 7/2018 | Monteleone et al. |
| 10,081,809 B2 | 9/2018 | Monteleone et al. |
| 10,272,047 B2 | 4/2019 | Baroni et al. |
| 10,337,004 B2 * | 7/2019 | Monteleone ......... C12N 15/113 |
| 10,443,056 B2 | 10/2019 | Monteleone et al. |
| 10,473,669 B2 | 11/2019 | Monteleone |
| 10,633,660 B2 | 4/2020 | Monteleone |
| 10,738,309 B2 | 8/2020 | Monteleone |
| 2005/0119203 A1 | 6/2005 | Steinbrecher et al. |
| 2007/0042985 A1 | 2/2007 | Monteleone et al. |
| 2007/0167385 A1 | 7/2007 | Monteleone et al. |

(Continued)

FOREIGN PATENT DOCUMENTS

| WO | WO 2016/059239 | 4/1916 |
| WO | WO 2016/059243 | 4/1916 |

(Continued)

OTHER PUBLICATIONS

Zorzi e al. AP&T Alimentary Pharmcology and Therapeutics 36, 850-857 (Year: 2012).*
Di Sabatino et al. Gut 58 777-789 (Year: 2009).*
International Search Report and Written Opinion dated Jul. 14, 2017 for PCT/US17/19094; 24 pages.
Adler et al., 2011, "Magnetization transfer helps detect intestinal fibrosis in an animal model of Crohn disease", Radiology, 259:127-135.
Lewis et al., 2015, "Intestinal fibrosis in Crohn's disease: role of microRNAs as fibrogenic modulators, serum biomarkers, and therapeutic targets", Inflammatory Bowel Diseases, 21(5):1141-1150.
Maccioni et al., 2012, "Value of T2-weighted magnetic resonance imaging in the assessment of wall inflammation and fibrosis in Crohn's disease", Abdominal Imaging, 37:944-957.

(Continued)

*Primary Examiner* — Brian Whiteman
(74) *Attorney, Agent, or Firm* — Goodwin Procter LLP

(57) ABSTRACT

The present invention relates to methods of treating, preventing or managing intestinal fibrosis by inhibiting SMAD7. The invention is also directed to methods of monitoring effectiveness of treatment or management of intestinal fibrosis using a SMAD7 antisense oligonucleotide, as well as methods of regulating SMAD7 antisense oligonucleotide treatment, based on analysis of Transforming Growth Factor-β (TGF-β) levels, α-Smooth Muscle Actin (a-SMA) levels, and/or phosphorylated Mothers Against Decapentaplegic Homolog 3 (p-SMAD3) levels.

12 Claims, 16 Drawing Sheets
Specification includes a Sequence Listing.

(56) References Cited

U.S. PATENT DOCUMENTS

| | | |
|---|---|---|
| 2009/0156539 A1 | 6/2009 | Monteleone et al. |
| 2009/0226460 A1* | 9/2009 | Phillips .............. A61K 31/4174 424/158.1 |
| 2010/0317719 A1 | 12/2010 | Monteleone et al. |
| 2011/0207795 A1 | 8/2011 | Steinbrecher et al. |
| 2012/0015033 A1 | 1/2012 | Baroni et al. |
| 2012/0136043 A1 | 5/2012 | Monteleone et al. |
| 2013/0203839 A1 | 8/2013 | Monteleone et al. |
| 2014/0142163 A1 | 5/2014 | Monteleone et al. |
| 2014/0256788 A1 | 9/2014 | Monteleone et al. |
| 2014/0271860 A1 | 9/2014 | Monteleone et al. |
| 2015/0087708 A1* | 3/2015 | Baroni ................. A61K 31/196 514/567 |
| 2015/0148245 A1 | 5/2015 | Monteleone et al. |
| 2015/0211011 A1 | 7/2015 | Monteleone et al. |
| 2015/0125523 A1 | 8/2015 | Monteleone et al. |
| 2015/0218561 A1 | 8/2015 | Monteleone et al. |
| 2015/0232854 A1 | 8/2015 | Baroni et al. |
| 2015/0315573 A1 | 10/2015 | Monteleone et al. |
| 2015/0337312 A1 | 11/2015 | Monteleone et al. |
| 2015/0352065 A1* | 12/2015 | Hanf .................... A61K 31/381 562/426 |
| 2016/0177306 A1 | 6/2016 | Monteleone et al. |
| 2016/0222383 A1 | 8/2016 | Baroni et al. |
| 2016/0304876 A1 | 10/2016 | Monteleone et al. |
| 2017/0107520 A1 | 4/2017 | Baroni et al. |
| 2017/0233736 A1 | 8/2017 | Monteleone et al. |
| 2017/0240893 A1 | 8/2017 | Monteleone et al. |
| 2017/0247695 A1 | 8/2017 | Cicala et al. |
| 2017/0253880 A1 | 9/2017 | Monteleone et al. |
| 2018/0030450 A1 | 2/2018 | Monteleone et al. |
| 2018/0128829 A1 | 5/2018 | Monteleone et al. |
| 2018/0180630 A1 | 6/2018 | Monteleone et al. |
| 2018/0289692 A1 | 10/2018 | Horan et al. |
| 2018/0338992 A1* | 11/2018 | McNulty ............ C12N 15/1136 |
| 2019/0100758 A1 | 4/2019 | Monteleone et al. |
| 2019/0112608 A1 | 4/2019 | Monteleone |
| 2019/0136237 A1 | 5/2019 | Monteleone et al. |
| 2019/0211336 A1 | 7/2019 | Monteleone et al. |
| 2019/0328770 A1 | 10/2019 | Monteleone et al. |
| 2019/0338283 A1 | 11/2019 | Monteleone |
| 2019/0374472 A1 | 12/2019 | Baroni et al. |
| 2020/0032264 A1 | 1/2020 | Bellinvia |
| 2020/0181622 A1 | 6/2020 | Monteleone |
| 2020/0237801 A1 | 7/2020 | Bellinvia et al. |
| 2020/0239884 A1 | 7/2020 | Monteleone et al. |
| 2020/0325480 A1 | 10/2020 | Monteleone |
| 2020/0392491 A1 | 12/2020 | Frank et al. |

FOREIGN PATENT DOCUMENTS

| | | |
|---|---|---|
| WO | WO 2016/105516 | 6/1916 |
| WO | WO 2017/055611 | 4/1917 |
| WO | WO 2017/059225 | 4/1917 |
| WO | WO 2017/147276 | 8/1917 |
| WO | WO 2017/144689 | 5/1918 |
| WO | WO 2018/122376 | 7/1918 |
| WO | WO 2019/023439 | 1/1919 |
| WO | WO 2003/037368 | 5/2003 |
| WO | WO 2004/087920 | 10/2004 |
| WO | WO 2010/054826 | 5/2010 |
| WO | WO 2013/037970 | 3/2013 |
| WO | WO 2013/158868 | 10/2013 |
| WO | WO 2014/140333 | 9/2014 |
| WO | WO 2015/011694 | 1/2015 |
| WO | WO 2015/169966 | 11/2015 |

OTHER PUBLICATIONS

Nylund et al., 2013, "Quantitative contrast-enhanced ultrasound comparison between inflammatory and fibrotic lesions in patients with Crohn's disease", Ultrasound Med Biol, 39:1197-1206.

Pazahr et al., 2013, "Magnetization transfer for the assessment of bowel fibrosis in patients with Crohn's disease: initial experience", Magn. Reson. Mat. Phys. Biol. Med., 26:291-301.

Quaia et al., 2012, "The value of small bowel wall contrast enhancement after sulfur hexafluoride-filled microbubble injection to differentiate inflammatory from fibrotic strictures in patients with Crohn's disease", Ultrasound Med Biol, 38:1324-1332.

Rieder et al., 2012, "Animal models of intestinal fibrosis: new tools for the understanding of pathogenesis and therapy of human disease", Amer J of Physiology—Gastrointestinal and Liver Physiology, 303(7):G786-G801.

Speca et al., 2012, "Cellular and Molecular Mechanisms of Intestinal Fibrosis", World J of Gastroenterology, 18(28):3635-3661.

Stedham et al., 2011, "Ultrasound elasticity imaging for detecting intestinal fibrosis and inflammation in rats and humans with Crohn's disease", Gastroenterology, 141:819-826.

European Search Report dated Sep. 18, 2019 for EP Pat. App. No. 17757196.5 (8 pages).

Latella et al., 2008, "Prevention of colonic fibrosis by Boswellia and Scutellaria extracts in rats with colitis induced by 2,4,5-trinitrobenzene sulphonic acid", European J of Clinical Investigation, 38(6):410-420.

Chen, G., et al., miR-195 plays a role in steroid resistance of ulcerative colitis by targeting Smad7, Biochem J, 471 (3): 357-367 (2015).

Izzo, R., et al., Knockdown of Smad7 with a specific antisense oligonucleotide attenuates colitis and colitis-driven colonic fibrosis in mice, Inflamm Bowel Dis, 24(6): 1213-1224 (2018).

Nakao, A., Smad7 and autoimmune/inflammatory disease, Molecular Rheumatism, 2(1): 22-27 (2005).

U.S. Appl. No. 17/162,226, filed Jan. 29, 2021.

* cited by examiner

Formula (I) – Page 1

Formula (I) – Page 2

Formula (I) – Page 3

Formula (I) – Page 4

METHODS OF TREATING INTESTINAL FIBROSIS USING SMAD7 INHIBITION

CROSS REFERENCE TO RELATED APPLICATIONS

This application is a U.S. National Stage Application under 35 U.S.C. § 371 of International Patent Application No. PCT/US2017/019094, filed on Feb. 23, 2017, under the Patent Cooperation Treaty (PCT), which claims the benefit of priority to U.S. Provisional Patent Application No. 62/298,988, filed on Feb. 23, 2016, the disclosure of which is incorporated by reference herein in its entirety.

SEQUENCE LISTING

This application incorporates by reference in its entirety the Computer Readable Form (CRF) of a Sequence Listing in ASCII text format submitted via EFS-Web. The Sequence Listing text file submitted via EFS-Web, entitled 14247-015-999_SEQ_LISTING.txt, was created on Aug. 17, 2018, and is 4,559 bytes in size.

FIELD OF THE INVENTION

The present invention relates to methods of treating, preventing or managing intestinal fibrosis by inhibiting Mothers Against Decapentaplegic Homolog 7 (SMAD7). The invention is also directed to methods of monitoring effectiveness of treatment or management of intestinal fibrosis using a SMAD7 antisense oligonucleotide, as well as methods of regulating SMAD7 antisense oligonucleotide treatment, based on analysis of Transforming Growth Factor-β (TGF-β) levels, α-Smooth Muscle Actin (α-SMA) levels, and/or phosphorylated Mothers Against Decapentaplegic Homolog 3 (p-SMAD3) levels.

BACKGROUND

Fibrosis is the formation of excess fibrous connective tissue in an organ or tissue in a reparative or reactive process, e.g., healing, usually because of injury or long-term inflammation. Fibrosis causes the affected tissues to harden and/or swell and reduces the flow of fluids through these tissues. As result, tissues with fibrosis may not be able to function properly.

Intestinal fibrosis is a common complication of inflammatory bowel disease (IBD) that can become symptomatic and may require surgical intervention if stricture formation ensues. Most of the traditional and novel mechanisms underlying intestinal fibrosis are associated with chronic inflammation.

SUMMARY

In one aspect, the invention is a method of treating, preventing or managing intestinal fibrosis or preventing collagen deposition, comprising inhibiting SMAD7 in a patient suffering from intestinal fibrosis or collagen deposition. The invention is also a method of treating, preventing or managing intestinal fibrosis or preventing collagen deposition, comprising inhibiting SMAD7 in a cell, for example, an intestinal cell. In yet another aspect, the invention is a method of treating, preventing or managing intestinal fibrosis or preventing collagen deposition in a patient, comprising administering to the patient an effective amount of a specific inhibitor of SMAD7.

In some embodiments, the patient suffering from intestinal fibrosis has previously suffered from inflammatory bowel disease or is suffering from inflammatory bowel disease, or inflammatory bowel disease preceded intestinal fibrosis in the patient. In some embodiments, the inflammatory bowel disease is Crohn's disease. In some embodiments, the inflammatory bowel disease is ulcerative colitis.

In some embodiments, the patient suffering from intestinal fibrosis previously suffered from colitis or is suffering from colitis, or colitis preceded intestinal fibrosis in the patient. In some embodiments, the colitis is acute colitis. In some embodiments, the colitis is chronic colitis.

In some embodiments of the invention the patient is a mammal, for example, a primate, for example, a human.

The invention relates in part to the fact that levels of p-SMAD3, α-SMA, and/or TGF-β in a patient with intestinal fibrosis correlate with intestinal fibrosis disease state and can be used as a means for monitoring disease state and managing responsiveness to intestinal fibrosis treatment with an anti-SMAD7 therapy. The invention is also that one can use monitoring and analysis of p-SMAD3, α-SMA, and/or TGF-β levels in a patient with intestinal fibrosis to determine appropriate levels of SMAD7 antisense oligonucleotide administration and to regulate and adjust SMAD7 antisense oligonucleotide treatment.

It will be appreciated that it is advantageous to be able to determine shortly after commencing treatment, shortly before stopping treatment, or shortly after stopping treatment, whether an intestinal fibrosis patient is responsive to treatment with an anti-SMAD7 therapy, in particular, a SMAD7 antisense oligonucleotide. Modulation of p-SMAD3, α-SMA, and/or TGF-β levels in a patient with intestinal fibrosis, as described herein, is useful for evaluating the efficacy of and responsiveness to treatment with an anti-SMAD7 therapy in a subject having intestinal fibrosis. Furthermore, it will be appreciated that it is advantageous to be able to evaluate and modulate administration of an anti-SMAD7 therapy in a patient with intestinal fibrosis based on levels, or changes in levels, of a biomarker, e.g., p-SMAD3, α-SMA, and/or TGF-β, that correlate with disease state. Thus, the invention provides methods for analyzing levels of p-SMAD3, α-SMA, and/or TGF-β in a patient being treated with or who has been administered an anti-SMAD7 therapy, e.g., a SMAD7 antisense oligonucleotide, and adjusting dosage levels based on p-SMAD3, α-SMA, and/or TGF-β levels or changes in p-SMAD3, α-SMA, and/or TGF-β levels determined by an analyzing step, following a dose of the anti-SMAD7 therapy. Advantageously, the methods of the invention will ultimately assist physicians in choosing effective therapies and monitoring and adjusting treatment with said therapies. Furthermore, methods of the invention will lead to improvements in intestinal fibrosis treatment efficacy for patients, with reduction in overall patient costs.

In a first aspect, the invention provides methods for treating, preventing or managing intestinal fibrosis in a patient having intestinal fibrosis. In one embodiment, the method includes the following steps: (a) administering to the patient an initial dose of a SMAD7 antisense oligonucleotide; (b) analyzing the level of p-SMAD3, α-SMA, or TGF-β in the patient; and (c) if the level of p-SMAD3, α-SMA, or TGF-β is above normal levels of p-SMAD3, α-SMA, or TGF-β, then administering to the patient a subsequent dose that is greater than or equal to the initial dose. Alternatively, if in step (c), the level of p-SMAD3, α-SMA, or TGF-β is below normal levels of p-SMAD3, α-SMA, or TGF-β as determined in step (b), then step (c)

includes administering to the patient a subsequent dose that is equal to or smaller than the initial dose.

In some embodiments, the invention may comprise a SMAD7 antisense oligonucleotide for use in a method of treating, preventing or managing intestinal fibrosis. For instance, in some embodiments, the invention comprises a SMAD7 antisense oligonucleotide for use in a method for treating, preventing or managing intestinal fibrosis in a patient having intestinal fibrosis, wherein the method comprises analyzing the level of p-SMAD3, α-SMA, or TGF-β in the patient to determine appropriate levels of SMAD7 antisense oligonucleotide administration. In some embodiments, the invention comprises a SMAD7 antisense oligonucleotide for this use, wherein the method comprises the steps of: (a) administering to the patient an initial dose of the SMAD7 antisense oligonucleotide; (b) analyzing the level of p-SMAD3, α-SMA, or TGF-β in the patient; and (c) if the level of p-SMAD3, α-SMA, or TGF-β is above normal levels of p-SMAD3, α-SMA, or TGF-β, then administering to the patient a subsequent dose of the SMAD7 antisense oligonucleotide that is greater than or equal to the initial dose, or, if the level of p-SMAD3, α-SMA, or TGF-β is below normal levels of p-SMAD3, α-SMA, or TGF-β, then administering to the patient a subsequent dose of the SMAD7 antisense oligonucleotide that is equal to or smaller than the initial dose.

In one embodiment, the invention comprises a SMAD7 antisense oligonucleotide for use in a method for treating, preventing or managing intestinal fibrosis in a patient having intestinal fibrosis, wherein the method comprises analyzing the level of TNF-α mRNA in the patient to determine appropriate levels of SMAD7 antisense oligonucleotide administration.

In another aspect of the invention, the invention provides methods for treating, preventing or managing intestinal fibrosis in a patient having intestinal fibrosis with respect to administration of an initial dose of a SMAD7 antisense oligonucleotide. In one embodiment, the invention provides a method for treating, preventing or managing intestinal fibrosis in a patient having intestinal fibrosis, where the method includes the following steps: (a) analyzing the level of p-SMAD3, α-SMA, or TGF-β in the patient; and (b) if the level of p-SMAD3, α-SMA, or TGF-β is above normal levels of p-SMAD3, α-SMA, or TGF-β, then administering to the patient an initial dose of a SMAD7 antisense oligonucleotide. In a particular embodiment, the invention provides a method for treating, preventing or managing intestinal fibrosis in a patient having intestinal fibrosis, where the method includes the following steps: (a) analyzing the level of p-SMAD3, α-SMA, or TGF-β in the patient; and (b) if the level of p-SMAD3, α-SMA, or TGF-β is above 0.01 pg/ml, 0.1 pg/ml, 1 pg/ml 2 pg/ml, 3 pg/ml, 4 pg/ml, 5 pg/ml, 6 pg/ml, 7 pg/ml, 8 pg/ml, 9 pg/ml, 10 pg/ml, 11 pg/ml, 12 pg/ml, 13 pg/ml, 14 pg/ml, 15 pg/ml, 17.5 pg/ml, 20 pg/ml, 22.5 pg/ml, 25 pg/ml, 30 pg/ml, or 35 pg/ml, then administering to the patient an initial dose of a SMAD7 antisense oligonucleotide.

Additionally, the method may further include the steps of: (c) analyzing the level of p-SMAD3, α-SMA, or TGF-β in the patient after said administering step, i.e., step (b); and (d) if the level of p-SMAD3, α-SMA, or TGF-β is above normal levels of p-SMAD3, α-SMA, or TGF-β, then administering to the patient a subsequent dose that is greater than or equal to the initial dose. Alternatively, if in step (d), the level of p-SMAD3, α-SMA, or TGF-β is below normal levels of p-SMAD3, α-SMA, or TGF-β, as determined in step (c), then step (d) includes administering to the patient a subsequent dose that is equal to or smaller than the initial dose. In some instances, if the subsequent dose administered in step (d) is equal to or greater than the maximum tolerated dose (MTD), then the method includes the step of terminating the treatment.

In some embodiments, the invention comprises methods of treating, preventing or managing intestinal fibrosis, dependent upon establishment of a control level of p-SMAD3, α-SMA, or TGF-β. For example, in a particular embodiment, the method for treating, preventing or managing intestinal fibrosis in a patient having intestinal fibrosis includes the steps of (a) establishing a control level of p-SMAD3, α-SMA, or TGF-β for the patient; (b) administering to the patient an initial dose of a SMAD7 antisense oligonucleotide; (c) analyzing the level of p-SMAD3, α-SMA, or TGF-β in the patient; and (d) if the level of p-SMAD3, α-SMA, or TGF-β is lower than the control level, then administering to the patient a subsequent dose that is the same as the initial dose or smaller than the initial dose. Alternatively, if the level of p-SMAD3, α-SMA, or TGF-β determined in step (c) is unchanged or increased compared to the control level, then the method includes a step (d) of administering to the patient a subsequent dose that is the same as the initial dose or greater than the initial dose or terminating the treatment.

In some embodiments, the method comprises the steps of (a) analyzing a first level of any of p-SMAD3, α-SMA, or TGF-β in the patient; (b) administering to the patient an initial dose of a SMAD7 antisense oligonucleotide (AON); and (c) analyzing a second level of p-SMAD3, α-SMA, or TGF-β in the patient after the administering step. In an embodiment of the invention, if the second level of p-SMAD3, α-SMA, or TGF-β is the same or higher than the first level of p-SMAD3, α-SMA, or TGF-β, then: administering to the patient a subsequent dose that is equal to or greater than the initial dose, and/or administering to the patient a subsequent dose at an equal or higher frequency than the initial dose. Alternatively, if the second level of p-SMAD3, α-SMA, or TGF-β is lower than the first level of p-SMAD3, α-SMA, or TGF-β, then administering to the patient a subsequent dose that is equal to or smaller than the initial dose, and/or administering to the patient a subsequent dose at an equal or lower frequency than the initial dose.

In some embodiments of the invention, the second level of p-SMAD3, α-SMA, or TGF-β is higher than the first level of p-SMAD3, α-SMA, or TGF-β. For example, in some embodiments, the second level of p-SMAD3, α-SMA, or TGF-β is about 10% higher, about 20% higher, about 30% higher, about 40% higher, about 50% higher, about 60% higher, about 70% higher, about 80% higher, about 90% higher, about 100% higher, or more than the first level of p-SMAD3, α-SMA, or TGF-β. In some embodiments, the second level of p-SMAD3, α-SMA, or TGF-β is about 10% to about 20% higher, about 20% to about 30% higher, about 30% to about 40% higher, about 40% to about 50% higher, about 50% to about 60% higher, about 60% to about 70% higher, about 70% to about 80% higher, about 80% to about 90% higher, or about 90% to about 100% higher than the first level of p-SMAD3, α-SMA, or TGF-β. Alternatively, in some embodiments, the second level of p-SMAD3, α-SMA, or TGF-β is lower than the first level of p-SMAD3, α-SMA, or TGF-β. For example, in some embodiments, the second level of p-SMAD3, α-SMA, or TGF-β is about 10% lower, about 20% lower, about 30% lower, about 40% lower, about 50% lower, about 60% lower, about 70% lower, about 80% lower, about 90% lower, or about 100% lower than the first level of p-SMAD3, α-SMA, or TGF-β. In some embodiments, the second level of p-SMAD3, α-SMA, or TGF-β is about 10% to about 20% lower, about 20% to about 30% lower, about 30% to about 40% lower, about 40% to about 50% lower, about 50% to about 60% lower, about 60% to about 70% lower, about 70% to about 80% lower, about 80% to about 90% lower, or about 90% to about 100% lower than the first level of p-SMAD3, α-SMA, or TGF-β.

In some embodiments, the invention comprises a method for treating, preventing or managing intestinal fibrosis in a patient having intestinal fibrosis, wherein the method comprises the steps of (a) administering to the patient an initial dose of a SMAD7 antisense oligonucleotide; and (b) analyzing the level of p-SMAD3, α-SMA, or TGF-β in the patient after the administering step. In some embodiments, if the level of p-SMAD3, α-SMA, or TGF-β is above normal levels of p-SMAD3, α-SMA, or TGF-β, then the patient is administered a subsequent dose that is greater than or equal to the initial dose, and/or administering to the patient a subsequent dose at an equal or higher frequency than the initial dose. In some embodiments, if the level of p-SMAD3, α-SMA, or TGF-β is below normal levels of p-SMAD3, α-SMA, or TGF-β, then the patient is administered a subsequent dose that is equal to or smaller than the initial dose and/or administering to the patient a subsequent dose at an equal or lower frequency than the initial dose.

In some embodiments of the invention, the level of p-SMAD3, α-SMA, or TGF-β is higher than the normal level of p-SMAD3, α-SMA, or TGF-β. For example, in some embodiments, the level of p-SMAD3, α-SMA, or TGF-β is about 10% higher, about 20% higher, about 30% higher, about 40% higher, about 50% higher, about 60% higher, about 70% higher, about 80% higher, about 90% higher, about 100% higher, or more than the normal level of p-SMAD3, α-SMA, or TGF-β. In some embodiments, the level of p-SMAD3, α-SMA, or TGF-β is about 10% to about 20% higher, about 20% to about 30% higher, about 30% to about 40% higher, about 40% to about 50% higher, about 50% to about 60% higher, about 60% to about 70% higher, about 70% to about 80% higher, about 80% to about 90% higher, or about 90% to about 100% higher than the normal level of p-SMAD3, α-SMA, or TGF-β. In some embodiments, the level of p-SMAD3, α-SMA, or TGF-β is lower than the normal level of p-SMAD3, α-SMA, or TGF-β. For example, in some embodiments, the level of p-SMAD3, α-SMA, or TGF-β is about 10% lower, about 20% lower, about 30% lower, about 40% lower, about 50% lower, about 60% lower, about 70% lower, about 80% lower, about 90% lower, or about 100% lower than the normal level of p-SMAD3, α-SMA, or TGF-β. In some embodiments, the second level of p-SMAD3, α-SMA, or TGF-β is about 10% to about 20% lower, about 20% to about 30% lower, about 30% to about 40% lower, about 40% to about 50% lower, about 50% to about 60% lower, about 60% to about 70% lower, about 70% to about 80% lower, about 80% to about 90% lower, or about 90% to about 100% lower than the normal level of p-SMAD3, α-SMA, or TGF-β.

In some embodiments, the invention comprises a SMAD7 antisense oligonucleotide for use in a method for treating, preventing or managing intestinal fibrosis in a patient having intestinal fibrosis, wherein the method comprises (a) analyzing the level of p-SMAD3, α-SMA, or TGF-β in the patient; and (b) if the level of p-SMAD3, α-SMA, or TGF-β is above normal levels of p-SMAD3, α-SMA, or TGF-β, then administering to the patient an initial dose of the SMAD7 antisense oligonucleotide.

The level of p-SMAD3, α-SMA, or TGF-β may be analyzed at varying time points following an administering step (b). For instance, in some embodiments, following an administering step (b), the level of p-SMAD3, α-SMA, or TGF-β is analyzed at least 1 day, at least 3 days, at least 5 days, at least 1 week, at least 2 weeks, at least 3 weeks, at least 1 month, at least 2 months, at least 4 months, or at least 6 months after said administration step. In some embodiments, the level of p-SMAD3, α-SMA, or TGF-β is analyzed immediately after said administration step. In yet other embodiments, the level of p-SMAD3, α-SMA, or TGF-β is analyzed about 7 days, about 10 days, about 15 days, about 20 days, about 25 days, or about 28 days after said administration step.

Normal levels or a control level of p-SMAD3, α-SMA, or TGF-β may be determined based on numerical reference values or with respect to levels of p-SMAD3, α-SMA, or TGF-β in a healthy control group. For instance, in some embodiments, a control level or normal levels of p-SMAD3, α-SMA, or TGF-β are about 0.01 pg/ml, about 0.1 pg/ml, about 1 pg/ml, about 2 pg/ml, about 3 pg/ml, about 4 pg/ml, about 5 pg/ml, about 6 pg/ml, about 7 pg/ml, about 8 pg/ml, about 9 pg/ml, about 10 pg/ml, about 11 pg/ml, about 12 pg/ml, about 13 pg/ml, about 14 pg/ml, about 15 pg/ml, about 16 pg/ml, about 17 pg/ml, about 17.5 pg/ml, about 18 pg/ml, about 19 pg/ml, about 20 pg/ml, about 22.5 pg/ml, about 25 pg/ml, about 30 pg/ml, or about 35 pg/ml. In other embodiments of the invention, a control level or normal levels of p-SMAD3, α-SMA, or TGF-β are defined as median levels of p-SMAD3, α-SMA, or TGF-β in a healthy control group. A healthy control group may be defined based on various criteria related to genetic background, habits, and physical attributes matched to the same set of criteria in the patient. For instance, in some embodiments, the healthy control group and the patient having intestinal fibrosis are matched with respect to age, gender, ethnic origin, smoking habits, dietary habits, body-mass index (BMI), recreational drug use, medical drug use, drug use related to intestinal fibrosis, and/or exercise habits. Other factors that can be matched between the patient and control group include, but are not limited to, clinical criteria (e.g., severity of intestinal fibrosis-related symptoms), metabolism, intestinal fibrosis patient's personal disease history, genetic factors, intestinal fibrosis patient's family disease history, exposure to environmental factors (e.g., pollutants, toxins, allergens), and life-style (e.g., urban, suburban, or rural place of work and/or domicile).

In various embodiments of the invention, the initial dose of a SMAD7 antisense oligonucleotide administered to a patient having intestinal fibrosis may vary. For instance, in some embodiments, the initial dose of a SMAD7 antisense oligonucleotide administered to a patient having intestinal fibrosis is less than 500 mg/day, less than 400 mg/day, less than 300 mg/day, less than 200 mg/day, less than 100 mg/day, less than 90 mg/day, less than 80 mg/day, less than 70 mg/day, less than 60 mg/day, less than 50 mg/day, less than 40 mg/day, less than 30 mg/day, less than 20 mg/day, or less than 10 mg/day. Alternatively, in other embodiments, the initial dose is at least 1 mg/day, at least 5 mg/day, at least 10 mg/day, at least 20 mg/day, at least 30 mg/day, at least 40 mg/day, at least 50 mg/day, at least 60 mg/day, at least 70 mg/day, at least 80 mg/day, at least 90 mg/day, at least 100 mg/day, at least 200 mg/day, at least 300 mg/day, at least 400 mg/day, or at least 500 mg/day. In yet other embodiments, the initial dose is about 5 mg/day, about 10 mg/day, about 20 mg/day, about 30 mg/day, about 40 mg/day, about 50 mg/day, about 60 mg/day, about 70 mg/day, about 80 mg/day, about 90 mg/day, about 100 mg/day, about 200 mg/day, about 300 mg/day, about 400 mg/day, or about 500 mg/day. In some embodiments, the initial dose is 5 mg/day, 10 mg/day, 20 mg/day, 30 mg/day, 40 mg/day, 50 mg/day, 60 mg/day, 70 mg/day, 80 mg/day, 90 mg/day, 100 mg/day, 110 mg/day, 120 mg/day, 130 mg/day, 140 mg/day, 150 mg/day, 160 mg/day, 170 mg/day, 180 mg/day, 190 mg/day, or 200 mg/day.

In some embodiments of the invention, after analyzing the level of p-SMAD3, α-SMA, or TGF-β in the patient in a step (b) or (c), if the level of p-SMAD3, α-SMA, and/or TGF-β is above normal levels of p-SMAD3, α-SMA, or TGF-β, then the method may include the step of administering to the patient a subsequent dose that is greater than the initial dose. In some embodiments, after analyzing the level of p-SMAD3, α-SMA, or TGF-β in the patient in a step (b) or (c), if the level of p-SMAD3, α-SMA, or TGF-β is below normal levels of p-SMAD3, α-SMA, or TGF-β, then the method may include the step of administering to the patient a subsequent dose that is smaller than the initial dose.

The invention also provides a method for determining the level of a subsequent dose of SMAD7 antisense oligonucleotide with respect to an initial dose of SMAD7 antisense oligonucleotide based on levels of p-SMAD3, α-SMA, or TGF-β in a patient having intestinal fibrosis. For instance, in embodiments of the invention described herein, if p-SMAD3, α-SMA, or TGF-β levels in a patient having intestinal fibrosis are above normal levels or a control level following an initial administration step (a) or (b), the subsequent dose administered in a step (c) or (d) is at least about 5 mg/day, at least about 10 mg/day, at least about 20 mg/day, at least about 30 mg/day, at least about 40 mg/day, at least about 50 mg/day, at least about 60 mg/day, at least about 70 mg/day, at least about 80 mg/day, at least about 90 mg/day, at least about 100 mg/day, at least about 110 mg/day, at least about 120 mg/day, at least about 130 mg/day, at least about 140 mg/day, at least about 150 mg/day, at least about 160 mg/day, at least about 170 mg/day, at least about 180 mg/day, at least about 190 mg/day, or at least about 200 mg/day greater than the initial dose.

Alternatively, in some embodiments, if p-SMAD3, α-SMA, or TGF-β levels in a patient having intestinal fibrosis are below a control level or normal levels following an initial administration step (a) or (b), the subsequent dose administered in a step (c) or (d) is at least about 5 mg/day, at least about 10 mg/day, at least about 20 mg/day, at least about 30 mg/day, at least about 40 mg/day, at least about 50 mg/day, at least about 60 mg/day, at least about 70 mg/day, at least about 80 mg/day, at least about 90 mg/day, or at least about 100 mg/day smaller than the initial dose. Furthermore, in some embodiments, the initial dose administered in an initial administration step (a) or (b) is between about 10 mg/day and 100 mg/day, about 5 mg/day and 200 mg/day, about 10 mg/day and 50 mg/day, about 50 mg/day and 100 mg/day, and about 100 mg/day and about 200 mg/day, and the subsequent dose administered in a step (c) or (d) is between about 30 mg/day and 200 mg/day, about 5 mg/day and 30 mg/day, about 20 mg/day and 50 mg/day, about 50 mg/day and 100 mg/day, or about 100 mg/day and 200 mg/day.

The invention also provides methods for modulating treatment with a SMAD7 antisense oligonucleotide in a patient with intestinal fibrosis based on a comparison of relative levels of p-SMAD3, α-SMA, or TGF-β in a patient before and after an initial administering step. The method includes the following steps: (a) analyzing the level of p-SMAD3, α-SMA, or TGF-β in the patient; and (b) if the level of p-SMAD3, α-SMA, or TGF-β is above normal levels of p-SMAD3, α-SMA, or TGF-β, then administering to the patient an initial dose of a SMAD7 antisense oligonucleotide; (c) analyzing the level of p-SMAD3, α-SMA, or TGF-β in the patient after said administering step; and (d) if the level of p-SMAD3, α-SMA, or TGF-β is lower after said administration step than the level of p-SMAD3, α-SMA, or TGF-β before said administration step, then administering to the patient a subsequent dose that is the same as the initial dose or smaller than the initial dose. Alternatively, in step (d) if the level of p-SMAD3, α-SMA, or TGF-β is unchanged or increased after said administration step (i.e., step (b)) compared to the level of p-SMAD3, α-SMA, or TGF-β before said administration step, then step (d) includes administering to the patient a subsequent dose that is greater than the initial dose or terminating the treatment.

According to methods of the invention, a change in p-SMAD3, α-SMA, or TGF-β levels observed after an initial administration step (of SMAD7 antisense oligonucleotide) compared to p-SMAD3, α-SMA, or TGF-β levels prior to the administration step can be compared, for example, as a change in percent of p-SMAD3, α-SMA, or TGF-β levels, to determine the amount of a subsequent dose of SMAD7 antisense oligonucleotide to be administered to a patient with intestinal fibrosis. For example, in some embodiments, if the level of p-SMAD3, α-SMA, or TGF-β is at least 10%, at least 20%, at least 30%, at least 40%, at least 50%, at least 60%, at least 70%, at least 80%, at least 90%, or at least 95% decreased after said administration step (e.g., an administration step (b)) compared to the level of p-SMAD3, α-SMA, or TGF-β before said administration step, then the method includes a step (e.g., an administration step (d)) of administering to the patient a subsequent dose that is the same as the initial dose or smaller than the initial dose.

In some embodiments, the invention provides a method of treating, preventing or managing intestinal fibrosis in a patient with above normal levels of p-SMAD3, α-SMA, or TGF-β, where the method includes administering to the patient a dose of SMAD7 antisense oligonucleotide. Furthermore, in some embodiments, the invention provides methods for treating, preventing or managing intestinal fibrosis in a patient who has above normal p-SMAD3, α-SMA, or TGF-β levels following administration of a dose of a SMAD7 antisense oligonucleotide, where the patient is administered a further dose of the SMAD7 antisense oligonucleotide that is greater than or equal to the prior dose. Similarly, in some embodiments, the invention provides methods for treating, preventing or managing intestinal fibrosis in a patient having intestinal fibrosis who has below normal p-SMAD3, α-SMA, or TGF-β levels following administration of a dose of SMAD7 antisense oligonucleotide. In the latter case, the method will include administering to the patient a further dose of the SMAD7 antisense oligonucleotide that is less than or equal to the prior dose. In some embodiments, administration of the SMAD7 antisense oligonucleotide to the patient is repeated until the levels of one or more biomarkers, e.g., p-SMAD3, α-SMA, or TGF-β, reach normal levels.

The invention also provides methods of treating, preventing or managing intestinal fibrosis in a patient having above normal levels of p-SMAD3, α-SMA, or TGF-β, where the amount of a SMAD7 antisense oligonucleotide administered to the patient is increased until p-SMAD3, α-SMA, or TGF-β levels in the patient decrease. In such embodiments, levels of SMAD7 antisense oligonucleotide administered to the patient may be increased until the level of p-SMAD3, α-SMA, or TGF-β in the patient decreases to about a normal level of p-SMAD3, α-SMA, or TGF-β or a below normal level of p-SMAD3, α-SMA, or TGF-β.

In some embodiments, the invention provides a method of monitoring the treatment or management of intestinal fibrosis in a patient with intestinal fibrosis, that includes analyzing p-SMAD3, α-SMA, or TGF-β levels in the patient following each SMAD7 antisense oligonucleotide administration. Utilizing these methods, the absence of a decrease in p-SMAD3, α-SMA, or TGF-β levels indicates that the treatment or management is not effective. In such embodiments, p-SMAD3, α-SMA, or TGF-β levels may be analyzed one time or multiple times, for instance, two times, three times, four times, about five times, about 10 times, about 15 times, about 20 times, or about 30 times, after each administration of SMAD7 antisense oligonucleotide. Furthermore, the timing of the measurement of p-SMAD3, α-SMA, or TGF-β levels may vary with respect to the time of SMAD7 oligonucleotide administration such that p-SMAD3, α-SMA, or TGF-β levels may be analyzed immediately after, about 1 hour after, about 3 hours after, about 6 hours after, about 12 hours after, about 1 day after, about 3 days after, about 1 week after, about 2 weeks after, and/or about 1 month after SMAD7 antisense oligonucleotide administration.

In order to determine levels of a biomarker or analyte, for example, p-SMAD3, α-SMA, or TGF-β, in a patient having intestinal fibrosis using the methods described herein, a sample may be obtained from the patient. Therefore, in some embodiments of the invention, the level of p-SMAD3, α-SMA, or TGF-β in the patient having intestinal fibrosis is determined in a sample obtained from the patient having intestinal fibrosis. Analytes other than or in addition to p-SMAD3, α-SMA, or TGF-β, for example, but not limited to p-SMAD3, α-SMA, TGF-β, Collagen I-III, Connective Tissue Growth Factor (CTGF), Interleukin-13 (IL-13), Mothers Against Decapentaplegic Homolog 2 (SMAD2), Mothers Against Decapentaplegic Homolog 3 (SMAD3), and/or Platelet-Derived Growth Factor (PDGF) may also be determined in methods of the invention. Thus, in some embodiments of the invention, the method includes determining a level, or multiple levels, of one or more additional analytes in the patient having intestinal fibrosis. Analytes of SMAD3 include RNA, DNA, and protein products of or derived from the SMAD3 gene, described by NCBI Reference Sequences: NC_000015.10, XM_011521559.1, and XM_011521560.1. Analytes of SMAD2 include RNA, DNA, and protein products of or derived from the SMAD2 gene, described by NCBI Reference Sequences: NC_000018.10, XM_006722451.2, XM_005258259.2, XM_011525985.1, XM_011525983.1, XM_011525984.1, and XM_011525986.1. Analytes of α-SMA include RNA, DNA, and protein products of or derived from the α-SMA gene, described by NCBI Reference Sequences: NC_000010.11 and XM_011540016.1. Analytes of TGF-β include RNA, DNA, and protein products of or derived from the TGF-β gene, described by NCBI Reference Sequences: NC_000019.10 and XM_011527242.1. Analytes of collagen I include RNA, DNA, and protein products of or derived from the collagen I gene, described by NCBI Reference Sequences: NC_000017.11, XM_011524341.1, XM_005257058.3, and XM_005257059.3. Analytes of collagen II include RNA, DNA, and protein products of or derived from the collagen II gene, described by NCBI Reference Sequences: NC_000012.12, XM_006719242.2, XM_011537932.1, XM_011537931.1, XM_011537929.1, XM_011537930.1, XM_011537934.1, XM_011537928.1, XM_011537933.1, and XM_011537935.1. Analytes of collagen III include RNA, DNA, and protein products of or derived from the collagen III gene, described by NCBI Reference Sequence: NC_000002.12. Analytes of IL-13 include RNA, DNA, and protein products of or derived from the IL-13 gene, described by NCBI Reference Sequence NC_000005.10. Analytes of CTGF include RNA, DNA, and protein products of or derived from the CTGF gene, described by NCBI Reference Sequence NC_000006.12. Analytes of PDGF include RNA, DNA, and protein products of or derived from the PDGF gene, described by NCBI Reference Sequences: NC_000007.14, XM_011515417.1, XM_011515415.1, XM_011515418.1, XM_011515416.1, and XM_011515419.1.

Samples containing analytes of interest, for example, p-SMAD3, α-SMA, TGF-β, Collagen I-III, CTGF, IL-13, SMAD2, SMAD3, and/or PDGF, obtained from the patient having intestinal fibrosis, may include blood, serum, plasma, or intestinal tissue samples. Samples may also include tissue samples such as, but not limited to, tissue, gastrointestinal, mucosal, submucosal, intestinal, esophageal, ileal, rectal, or lymphatic samples. Levels of analytes of interest in a sample from a patient having intestinal fibrosis may be determined using various assays. For example, in methods of the invention, the level of p-SMAD3, α-SMA, or TGF-β and/or another analyte may be determined by immunochemistry, for example, by an enzyme-linked immunosorbent assay (ELISA), or by nucleotide analysis.

It will be appreciated that the SMAD7 antisense oligonucleotide administered to the patient having intestinal fibrosis in methods of the invention described herein, may be administered by various administration routes. In various embodiments, the SMAD7 antisense oligonucleotide may be administered by one or several routes, including orally, topically, parenterally, e.g., by subcutaneous injection, by inhalation spray, or rectally. The term parenteral as used herein includes subcutaneous injections, intrapancreatic administration, and intravenous, intramuscular, intraperitoneal, and intrasternal injection or infusion techniques. In a preferred embodiment, the SMAD7 antisense oligonucleotide may be administered orally to the patient having intestinal fibrosis.

The contemplated invention provides methods that include administration of a SMAD7 antisense oligonucleotide capable of targeting SMAD7 RNA for degradation, interfering with RNA splicing or preventing SMAD7 gene expression or protein translation. The contemplated SMAD7 antisense oligonucleotide of the invention may target various regions of the human SMAD7 mRNA for binding. For example, the SMAD7 antisense oligonucleotide may target nucleotides 108-128 of human SMAD7 mRNA (SEQ ID NO: 1). In some embodiments, the SMAD7 antisense oligonucleotide may target nucleotides 403, 233, 294, 295, 296, 298, 299 or 533 of the human SMAD7 sequence (SEQ ID NO: 1). The human SMAD7 mRNA sequence is the sequence of NCBI Reference Sequence: NM_005904.3 (SEQ ID NO: 1).

The sequence of the contemplated SMAD7 antisense oligonucleotide may be selected from multiple sequences capable of targeting SMAD7 RNA. For example, in some embodiments of the invention, the SMAD7 antisense oligonucleotide comprises the nucleotide sequence of SEQ ID NO: 2 (5'-GTCGCCCCTTCTCCCCGCAGC-3'). In some embodiments of the invention, the antisense oligonucleotide is an antisense oligonucleotide phosphorothioate, i.e., an oligonucleotide where at least some of the internucleotide linkages are phosphorothioate linkages, suitable for delivery to cells of a patient. Additionally, antisense oligonucleotides of the invention may include modified nucleotides, for example, nucleotides containing modified bases, for example, 5-methyl-2'-deoxycytidine. For example, in some embodiments, the antisense oligonucleotide is a SMAD7 antisense oligonucleotide phosphorothioate comprising the following sequence: 5'-GTXGCCCCTTCTCCCXGCAG-3' (SEQ ID NO: 3) wherein X is a nucleotide comprising 5-methyl-2'-deoxycytidine and wherein the internucleotide linkages are phosphorothioate linkages. In some embodiments, the antisense oligonucleotide is a SMAD7 antisense oligonucleotide phosphorothioate comprising the following sequence: 5'-GTXGCCCCTTCTCCCXGCAGC-3' (SEQ ID NO: 4) wherein X is a nucleotide comprising 5-methyl-2'-deoxycytidine and wherein the internucleotide linkages are phosphorothioate linkages. In a particular embodiment, the contemplated antisense oligonucleotide is an antisense oligonucleotide (referred to herein as "Mongersen") comprising the free acid form, the salt form or the anionic form without a counterion of SEQ ID NO: 4, wherein each of the 20 internucleotide linkages is an O,O-linked phosphorothioate linkage and shown in FIG. 9. In some embodiments, the phosphorothioate backbone of SEQ ID NO: 4 can be fully or partially protonated to form an acidic form of SEQ ID NO: 4. In some embodiments, the contemplated salts of SEQ ID NO: 4 include those that are fully neutralized, e.g., each phosphorothioate linkage is associated with an ion such as $Na^+$. In some embodiments the salts of SEQ ID NO: 4 are only partially neutralized, e.g., less than all phosphorothioate linkages are associated with an ion (e.g., less than 99%, less than 95%, less than 90%, less than 85%, less than 80%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 3%, or less than 1% are neutralized).

In some embodiments of the invention, a method of treating, preventing or managing intestinal fibrosis or preventing collagen deposition in a patient includes administering a pharmaceutical composition, for example, a pharmaceutical composition comprising a specific inhibitor of SMAD7, for example, a SMAD7 antisense oligonucleotide, and a pharmaceutically acceptable carrier. In some embodiments, the pharmaceutical composition is administered parenterally. In some embodiments, the pharmaceutical composition is administered orally. In some embodiments, the pharmaceutical composition includes an enteric coating, for example, an enteric coating comprising an ethylacrylate-methacrylic acid copolymer.

In embodiments of the invention, methods of treating, preventing or managing intestinal fibrosis or preventing collagen deposition in a patient include administering varying amounts of a SMAD7 antisense oligonucleotide or a pharmaceutical composition comprising a SMAD7 antisense oligonucleotide. In some embodiments, methods of the invention include administering at least 1 μg, at least 5 μg, at least 10 μg, at least, 20 μg, at least 30 μg, at least, 40 μg, at least, 50 μg, at least, 60 μg, at least 70 μg, at least, 80 μg, at least, 90 or at least 100 μg of the antisense oligonucleotide. In some embodiments, methods of the invention include administering from 35 mg to 500 mg, from 1 mg to 10 mg, from 10 mg to 20 mg, from 20 mg to 30 mg, from 30 mg to 40 mg, from 40 mg to 50 mg, from 50 mg to 60 mg, from 60 mg to 70 mg, from 70 mg to 80 mg, from 80 mg to 90 mg, from 90 mg to 100 mg, from 100 mg to 150 mg, from 150 mg to 200 mg, from 200 mg to 250 mg, from 250 mg to 300 mg, from 300 mg to 350 mg, from 350 mg to 400 mg, from 400 mg to 450 mg, from 450 mg to 500 mg, from 500 mg to 600 mg, from 600 mg to 700 mg, from 700 mg to 800 mg, from 800 mg to 900 mg, from 900 mg to 1 g, from 1 mg to 50 mg, from 20 mg to 40 mg, or from 1 mg to 500 mg of the antisense oligonucleotide.

DETAILED DESCRIPTION

Figure 1:
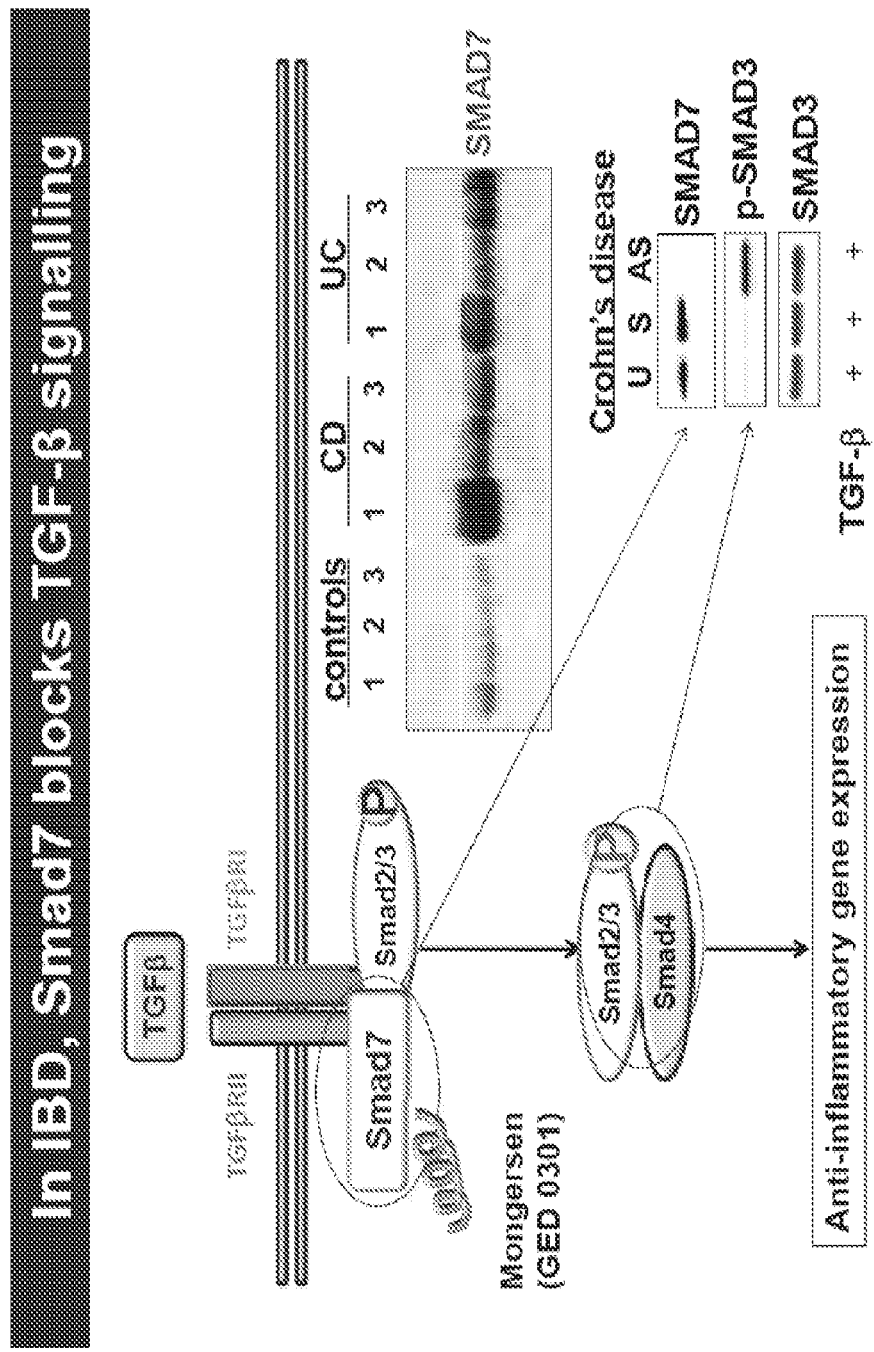
FIG. 1. Blockage by Smad7 of TGF-β signaling in Inflammatory Bowel Disease (IBD).

The invention provides methods that are generally useful for treating, preventing or managing intestinal fibrosis in a patient having intestinal fibrosis. The method is particularly useful in terms of managing treatment in a patient being treated with an anti-SMAD7 therapy, such as a SMAD7 antisense oligonucleotide therapy. A SMAD7 antisense oligonucleotide therapy may be any therapy that includes an oligonucleotide that is capable of binding to a SMAD7 mRNA transcript and inducing degradation of the SMAD7 mRNA transcript, preventing splicing of the SMAD7 mRNA transcript, or preventing protein translation of the SMAD7 mRNA transcript.

Methods of the invention are useful for predicting and determining responsiveness of patients having intestinal fibrosis to treatment with SMAD7 antisense oligonucleotide. Thus, methods of the invention can be used to identify patients that are likely to respond to SMAD7 antisense oligonucleotide treatment as well as patients that are unlikely to respond to SMAD7 antisense oligonucleotide treatment. The methods described herein are also useful for determining whether a patient is or is not responsive to intestinal fibrosis treatment. Generally, methods of the invention can also be used to determine the level or likely level of responsiveness in a patient having intestinal fibrosis being treated with a SMAD7 antisense oligonucleotide. Based upon a determination of a level of responsiveness or a likely level of responsiveness, administration of the SMAD7 antisense oligonucleotide may be initiated, repeated, maintained, increased, decreased, or terminated. Responsiveness may be determined using a number of factors including, but not limited to: analysis of levels or changes in levels of biomarkers and/or other analytes (e.g., TGF-β, α-SMA, and p-SMAD3), or assessment of symptoms of intestinal fibrosis (e.g., weight loss, tissue inflammation).

Similarly, the methods are useful for evaluating efficacy and safety of treatment with a SMAD7 antisense oligonucleotide in a patient having intestinal fibrosis. For example, methods of the invention may include determining changes in levels of biomarker expression or other indicators or manifestations of disease state that can indicate that treatment with the SMAD7 antisense oligonucleotide is effective or not effective to cause partial or complete amelioration of intestinal fibrosis. Determining levels or changes in levels of biomarker expression, disease symptoms, tissue, blood, or systemic levels of the SMAD7 antisense oligonucleotide, or indicators of general health may also indicate a worsening of disease state or unsafe drug levels. Assessment of multiple indicators before, during, between, and/or after treatment(s) may be used to monitor disease stage, progression, and severity.

The invention is based in part on the discovery of a relationship between intestinal fibrosis disease state and p-SMAD3, α-SMA, and TGF-β levels. Specifically, the inventors have discovered that each of p-SMAD3, α-SMA, and TGF-β levels is a useful biomarker for determining whether a patient is responsive to, likely to be responsive to, not responsive to, or likely not responsive to treatment of intestinal fibrosis using a SMAD7 antisense oligonucleotide.

Furthermore, p-SMAD3, α-SMA, or TGF-β levels can be used to manage disease treatment using a SMAD7 antisense oligonucleotide, specifically with respect to dose amount of the SMAD7 antisense oligonucleotide. For example, levels of p-SMAD3, α-SMA, or TGF-β may be used to determine whether a patient having intestinal fibrosis should be given a specific dose amount, for example, a higher dose or a lower dose, of SMAD7 antisense oligonucleotide, for example in a subsequent dose, with respect to, for example, a previously administered dose, for example, an initial dose, of SMAD7 antisense oligonucleotide. Thus, administration of a SMAD7 antisense oligonucleotide may be adjusted in terms of, for example, dose amount or frequency, with respect to absolute levels of p-SMAD3, α-SMA, or TGF-β or relative levels of p-SMAD3, α-SMA, or TGF-β in a patient having intestinal fibrosis. For instance, administration of a SMAD7 antisense oligonucleotide may be adjusted based on absolute levels of p-SMAD3, α-SMA, or TGF-β by comparing absolute levels of p-SMAD3, α-SMA, or TGF-β measured in a sample from a patient having intestinal fibrosis with a normal level of p-SMAD3, α-SMA, or TGF-β, where the normal level of p-SMAD3, α-SMA, or TGF-β is, for instance, either a benchmark value or a median level of p-SMAD3, α-SMA, or TGF-β in a healthy control group matched to the patient having intestinal fibrosis. In some embodiments of the invention, administration of a SMAD7 antisense oligonucleotide may be adjusted based on relative levels of p-SMAD3, α-SMA, or TGF-β, for instance, based on a comparison of p-SMAD3, α-SMA, or TGF-β levels before and after SMAD7 antisense oligonucleotide administration, immediately after and later after SMAD7 antisense oligonucleotide administration, or during and after SMAD7 antisense oligonucleotide administration. In some embodiments, the SMAD7 antisense oligonucleotide may be administered multiple times between an initial detection of p-SMAD3, α-SMA, or TGF-β levels and a later detection of p-SMAD3, α-SMA, or TGF-β levels used to generate the comparison of p-SMAD3, α-SMA, or TGF-β levels in the patient sample.

In some embodiments of the invention the intestinal fibrosis patient being treated is a patient with above-normal p-SMAD3, α-SMA, or TGF-β levels. In some embodiments, a patient is known to have high p-SMAD3, α-SMA, and/or TGF-β levels before treatment. In some embodiments, p-SMAD3, α-SMA, and/or TGF-β levels in the intestinal fibrosis patient are determined before treatment, after treatment, before administration of an initial dose of a SMAD7 antisense oligonucleotide, after administration of an initial dose of a SMAD7 antisense oligonucleotide, before administration of a subsequent dose of a SMAD7 antisense oligonucleotide, and/or after administration of a subsequent dose of a SMAD7 antisense oligonucleotide.

Control Levels and Control Samples

A control level of p-SMAD3, α-SMA, or TGF-β may be determined by determining the level of p-SMAD3, α-SMA, or TGF-β protein or mRNA transcript in a sample (e.g., a blood sample) obtained from the subject prior to treatment with an anti-SMAD7 therapy. The control level of p-SMAD3, α-SMA, or TGF-β may provide a baseline for monitoring a subject's response to treatment. A control sample may be obtained from the subject on the day the anti-SMAD7 therapy is first administered (e.g., Day 1 of a treatment regimen), for example, immediately after administration of at least one anti-SMAD7 therapy. In other embodiments, a control sample may be obtained from a subject one day prior to the start of an anti-SMAD7 therapy (e.g., Day 0 of a treatment regimen). Alternatively, a control sample may be obtained from a subject 2, 3, 4, 5, 6, 7 or more days prior to the start of an anti-SMAD7 therapy. For example, the increase or decrease in p-SMAD3, α-SMA, or TGF-β concentration may be measured prior to treatment (e.g., in a control sample), during treatment, and/or after treatment to monitor a subject's response to therapy, e.g., an anti-SMAD7 therapy.

In some embodiments, a control level may be established for a subject based on long-term monitoring of circulating p-SMAD3, α-SMA, or TGF-β concentration in the subject. In such instances, it is contemplated that a subject may undergo multiple rounds of treatment with an anti-SMAD7 therapy. The circulating p-SMAD3, α-SMA, or TGF-β concentration detected following multiple rounds of treatment may be compared to a prior control level of p-SMAD3, α-SMA, or TGF-β for the subject to determine whether the subject has responded to therapy and/or is likely to respond to further treatment with an anti-SMAD7 therapy. In other embodiments, a control or baseline level for a subject may be established based on an average measurement of a circulating p-SMAD3, α-SMA, or TGF-β concentration determined from multiple baseline samples obtained over time (e.g., obtained over the course of days, weeks, months, or years). Accordingly, any test or assay conducted as disclosed herein may be compared with a previous or established control level and it may not be necessary to obtain a new control sample from the subject for comparison, e.g., if the subject is receiving more than one round of treatment with an anti-SMAD7 therapy.

Normal levels of p-SMAD3, α-SMA, or TGF-β may be determined based on numerical reference values or with respect to levels of p-SMAD3, α-SMA, or TGF-β in a healthy control group.

In other embodiments of the invention, normal levels of p-SMAD3, α-SMA, or TGF-β are defined as median levels of p-SMAD3, α-SMA, or TGF-β in a healthy control group.

A healthy control group may be defined based on various criteria related to genetic background, habits, and physical attributes matched to the same set of criteria in the patient. For instance, in some embodiments, the healthy control group and the patient having intestinal fibrosis are matched with respect to age, gender, ethnic origin, smoking habits, dietary habits, body-mass index (BMI), recreational drug use, medical drug use, drug use related to intestinal fibrosis, and/or exercise habits. Other factors that can be matched between the patient and control group include, but are not limited to, clinical criteria (e.g., severity of intestinal fibrosis-related symptoms), metabolism, intestinal fibrosis patient's personal disease history, genetic factors, intestinal fibrosis patient's family disease history, exposure to environmental factors (e.g., pollutants, toxins, allergens), and life-style (e.g., urban, suburban, or rural place of work and/or domicile).

In some embodiments, the control group is the patient receiving a treatment with an SMAD7 antisense oligonucleotide prior to receiving an initial dose of the SMAD7 antisense oligonucleotide. In some embodiments, the patient is a treatment naive patient.

Data Interpretation

In some embodiments, prior to initial administration of an anti-SMAD7 therapy, the level of p-SMAD3, α-SMA, or TGF-β in a patient having intestinal fibrosis is analyzed and compared to a threshold level. As described herein, a threshold level may be established based on p-SMAD3, α-SMA, or TGF-β levels in a healthy control group or a group of intestinal fibrosis patients. In general, a threshold level will be elevated with respect to normal p-SMAD3, α-SMA, or TGF-β levels, for example median p-SMAD3, α-SMA, or TGF-β levels in a healthy control group, or it may fall within the spectrum of p-SMAD3, α-SMA, or TGF-β levels in a control group, for example a control group comprised of intestinal fibrosis patients.

A subject's responsiveness to treatment with an anti-SMAD7 therapy can be interpreted with respect to the control level of p-SMAD3, α-SMA, or TGF-β in a sample obtained from the subject prior to treatment. A subject may be identified as sensitive to treatment (e.g., responsive or likely to respond to treatment) with an anti-SMAD7 therapy if there is a decrease in the concentration of p-SMAD3, α-SMA, or TGF-β in the sample obtained from the subject compared to the control sample. In some embodiments the sample may be obtained while the subject is receiving an anti-SMAD7 therapy treatment. In other embodiments, the sample may be obtained after the subject has stopped receiving treatment, for example, about 1 day, about 7 days (i.e., about 1 week), about 14 days (i.e., about 2 weeks), about 28 days, about 56 days, about 70 days and/or longer, after stopping treatment. In a preferred embodiment, the sample may be obtained about one day after stopping anti-SMAD7 therapy treatment.

In some embodiments, patients receiving an anti-SMAD7 therapy, such as a SMAD7 antisense oligonucleotide, also receive one or more additional intestinal fibrosis therapies. In some embodiments, patients receiving the anti-SMAD7 therapy and the one or more additional intestinal fibrosis therapies can taper the one or more additional intestinal fibrosis therapies if they respond to the anti-SMAD7 therapy, e.g., as indicated by decreasing p-SMAD3, α-SMA, or TGF-β levels.

Alternatively, a subject may be identified as resistant to treatment (e.g., non-responsive or unlikely to respond) with an anti-SMAD7 therapy if there is no change or an increase in circulating p-SMAD3, α-SMA, or TGF-β concentration in the sample obtained from the subject, compared to the control level. In one embodiment, the sample may be obtained while the subject is receiving an anti-SMAD7 therapy treatment. In other embodiments, the sample may be obtained after the subject has stopped receiving treatment, for example, about 1 day, about 7 days (i.e., about 1 week), about 14 days (i.e., about 2 weeks), about 28 days, about 56 days, about 70 days, and/or longer after stopping treatment. In a preferred embodiment, the sample may be obtained about one day after stopping anti-SMAD7 therapy treatment.

In some embodiments, one or more rescue therapies (e.g., a biologic such as an p-SMAD3, α-SMA, or TGF-β inhibitor and/or an immunosuppressive drug) is administered to patients experiencing a worsening of disease during a course of treatment with an anti-SMAD7 therapy, e.g., as indicated by increasing increasing p-SMAD3, α-SMA, or TGF-β levels (e.g., >50% increase in p-SMAD3, α-SMA, or TGF-β levels).

Differences in patient p-SMAD3, α-SMA, or TGF-β levels and threshold p-SMAD3, α-SMA, or TGF-β levels are indicative of a patient's potential responsiveness to anti-SMAD7 therapy. For example, patient p-SMAD3, α-SMA, or TGF-β levels that are elevated relative to a threshold p-SMAD3, α-SMA, or TGF-β level indicate that a patient may be responsive to anti-SMAD7 therapy. Threshold levels of p-SMAD3, α-SMA, or TGF-β can be established using different criteria. In some embodiments, the threshold level of p-SMAD3, α-SMA, or TGF-β is determined with respect to normal p-SMAD3, α-SMA, or TGF-β levels, for example median p-SMAD3, α-SMA, or TGF-β levels, in a control group. Control groups may be comprised of healthy/normal subjects (e.g., a healthy control group) or groups of intestinal fibrosis patients.

For instance, in some embodiments, a p-SMAD3, α-SMA, or TGF-β threshold level is at least 2-fold, at least 3-fold, at least 5-fold, at least 8-fold, at least 10-fold, at least 20-fold, at least 30-fold, at least 50-fold, at least 80-fold, or at least 100-fold above normal levels. In other embodiments, the p-SMAD3, α-SMA, or TGF-β threshold level is in the $50^{th}$ percentile, $60^{th}$ percentile, $70^{th}$ percentile, $80^{th}$ percentile or $90^{th}$ percentile of p-SMAD3, α-SMA, or TGF-β levels with respect to p-SMAD3, α-SMA, or TGF-β levels, for example median p-SMAD3, α-SMA, or TGF-β levels, in a group of intestinal fibrosis patients. Additionally, in some embodiments, the threshold level of p-SMAD3, α-SMA, or TGF-β is at least or about 1 pg/ml, at least or about 2.5 pg/ml, at least or about 5 pg/ml, at least or about 7.5 pg/ml, at least or about 10 pg/ml, at least or about 12.5 pg/ml, at least or about 15 pg/ml, at least or about 17.5 pg/ml, at least or about 20 pg/ml, at least or about 25 pg/ml, at least or about 30 pg/ml, at least or about 35 pg/ml, at least or about 40.0 mg/L, or at least or about 45.0 mg/L (e.g., as measured in blood serum).

In some embodiments, the control group may consist of the patient receiving an initial dose of a SMAD7 antisense oligonucleotide. In some embodiments, normal p-SMAD3, α-SMA, or TGF-β levels, or p-SMAD3, α-SMA, or TGF-β threshold levels, may be the p-SMAD3, α-SMA, or TGF-β baseline levels that are observed in a patient prior to administration of an initial dose of SMAD7 antisense oligonucleotide. p-SMAD3, α-SMA, or TGF-β levels can subsequently be monitored in a patient over time, following the administration of the initial dose or of subsequent doses of SMAD7 antisense oligonucleotide to the patient. p-SMAD3, α-SMA, or TGF-β levels in the patient following one or more administrations of a SMAD7 antisense oligonucleotide can be compared to the p-SMAD3, α-SMA, or TGF-β baseline level in the patient. Dosing regimens for the SMAD7 antisense oligonucleotide can be adjusted, depending on whether p-SMAD3, α-SMA, or TGF-β levels in the patient increase, decrease or remain constant relative to the patient's p-SMAD3, α-SMA, or TGF-β baseline level.

Anti-SMAD7 Therapies

The present disclosure is directed in part to methods of treating, preventing or managing intestinal fibrosis in a patient with an anti-SMAD7 therapy comprising a SMAD7 inhibitor. SMAD7 inhibitors may include, for example, small binding molecules, e.g., natural and synthetic compounds, antibodies, aptamers, intramers, RNAi (double stranded RNA, siRNA) and SMAD7 antisense oligonucleotides that bind, degrade, or otherwise interfere with SMAD7 stability, production, or function. SMAD7 inhibitors may also comprise truncated and/or mutated SMAD7 molecules which interfere with SMAD7 activity, binding partners, or substrates and which, thereby, inhibit SMAD7 function.

The present disclosure is also directed in part to methods of treating, preventing or managing intestinal fibrosis in a patient with a SMAD7 antisense oligonucleotide. Antisense oligonucleotides are short synthetic oligonucleotide sequences complementary to the messenger RNA (mRNA), which encodes for the target protein (e.g., SMAD7). Antisense oligonucleotide sequences hybridize to the mRNA producing a double-strand hybrid that can lead to the activation of ubiquitary catalytic enzymes, such as RNase H, which degrades DNA/RNA hybrid strands thus preventing protein translation.

The contemplated SMAD7 antisense oligonucleotide may target any region of the SMAD7 mRNA. In certain embodiments, an anti-SMAD7 antisense oligonucleotide may target site 403, 233, 294, 295, 296, 298, 299, and/or 533 (i.e., nucleotides 403, 233, 294, 295, 296, 298, 299, and 533, respectively) of the human SMAD7 mRNA (e.g., of SEQ ID NO: 1; NCBI Reference Sequence NM_005904.3).

In certain embodiments, an antisense oligonucleotide may be derived from the following anti-SMAD7 antisense oligonucleotide 5'-GTCGCCCCTTCTCCCCGCAGC-3' (SEQ ID NO: 2).

It is contemplated herein that an antisense oligonucleotide targeting SMAD7 may comprise a mixed-backbone wherein the cytosine residues in a CpG pair are replaced by 5'-methylcytosine (abbreviated as Me-dC). Methylphosphonate linkages may also be placed at the 5' and/or 3' ends of an antisense oligonucleotide (abbreviated as MeP).

Exemplary antisense oligonucleotide therapies that target SMAD7 include, but are not limited to, 5'-GTXYCCCCTTCTCCCXYCAG-3' (SEQ ID NO: 5), wherein X is a nucleotide comprising a nitrogenous base selected from the group consisting of cytosine and 5-methylcytosine or a 2'-O-methylcytosine nucleoside, and wherein Y is a nucleotide comprising a nitrogenous base selected from the group consisting of guanine and 5-methylguanine or a 2'-O-methylguanine nucleoside, provided that at least one of the nucleotides X or Y comprises a methylated nitrogenous base;

5'-GTXGCCCCTTCTCCCXGCAG-3' (SEQ ID NO: 3), wherein X is 5-methyl 2'-deoxycytidine (See, e.g., U.S. Pat. Nos. 7,807,818 and 6,159,697, which are each incorporated herein by reference);

5'-GTXGCCCCTTCTCCCXGCAGC-3' (SEQ ID NO: 4), wherein X is 5-methyl 2'-deoxycytidine; and Antisense oligonucleotides described in U.S. Pat. No. 8,648,186 and International Patent Application Publication WO 2010/054826, each of which is incorporated herein by reference.

Contemplated antisense oligonucleotides include those comprising SEQ ID NO: 4: 5'-GTXGCCCCTT CTCCCXGCAGC-3', where X represents 5-methyl-2'-deoxycytidine. In some embodiments, at least one of the internucleotide linkages of a contemplated antisense oligonucleotide is an O,O-linked phosphorothioate, for example, each of the 20 internucleotide linkages of SEQ ID NO: 4 may be an O,O-linked phosphorothioate. In a particular embodiment, the contemplated antisense oligonucleotide is an antisense oligonucleotide (referred to herein as "Mongersen") comprising the free acid form, the salt form or the anionic form without a counterion of SEQ ID NO: 4, wherein each of the 20 internucleotide linkages is an O,O-linked phosphorothioate linkage and shown in FIG. 9. In some embodiments, contemplated compositions disclosed herein may include a pharmaceutically acceptable salt, e.g., a sodium salt of the antisense oligonucleotide of SEQ ID NO: 4, that optionally may include 1 to 20 O,O-linked phosphorothioate internucleotide linkages. Contemplated salts of antisense oligonucleotides include those that are fully neutralized, e.g., each phosphorothioate linkage is associated with an ion such as Na⁺. In some embodiments, the phosphorothioate backbone of SEQ ID NO: 4 can be fully or partially protonated to form an acidic form of SEQ ID NO: 4. In some embodiments, the contemplated salts of SEQ ID NO: 4 include those that are fully neutralized, e.g., each phosphorothioate linkage is associated with an ion such as Na⁻. In some embodiments, the contemplated salts of SEQ ID NO: 4 are only partially neutralized, e.g., less than all phosphorothioate linkages are associated with an ion (e.g., less than 99%, less than 95%, less than 90%, less than 85%, less than 80%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 3%, or less than 1% are neutralized). Oligonucleotides may include naturally occurring nucleobases, sugars, and covalent internucleotide (backbone) linkages as well as non-naturally occurring portions. In varying embodiments, the antisense oligonucleotides described herein, for example, the antisense oligonucleotides of SEQ ID NO: 2, SEQ ID NO: 3, and SEQ ID NO: 4, may include nucleotides comprising deoxycytidine and/or 5-methyl 2'-deoxycytidine, including, but not limited to, 5-methyl-2'-deoxycytidine 5'-monophosphate and 5-methyl-2'-deoxycytidine 5' monophosphorothioate.

Contemplated SMAD7 antisense oligonucleotides include oligonucleotides that act against SMAD7 and may be administered orally. Disclosed therapies may, when administered orally to a subject suffering from intestinal fibrosis, deliver an effective amount of an antisense oligonucleotide to the intestinal system of a patient, e.g., deliver an effective amount of an antisense oligonucleotide to the terminal ileum and/or right colon of a patient.

In some embodiments of the invention, the anti-SMAD7 therapy (i.e., a therapy comprising a SMAD7 antisense oligonucleotide) may be suitable for oral delivery of an antisense oligonucleotide, e.g., tablets, that include an enteric coating, e.g., a gastro-resistant coating, such that the compositions may deliver the antisense compound to, e.g., the terminal ileum and right colon of a patient. For example, such administration may result in a topical effect, substantially topically applying the antisense compound directly to an affected portion of the intestine of a subject. Such administration, may, in some embodiments, substantially avoid unwanted systemic absorption of the antisense compound.

For example, a tablet for oral administration may comprise granules (e.g., is at least partially formed from granules) that include a disclosed antisense compound and pharmaceutically acceptable excipients. Such a tablet may be coated with an enteric coating. Contemplated tablets may include pharmaceutically acceptable excipients such as fillers, binders, disintegrants, and/or lubricants, as well as coloring agents, release agents, coating agents, sweetening, flavoring such as wintergreen, orange, xylitol, sorbitol, fructose, and maltodextrin, and perfuming agents, preservatives and/or antioxidants.

In some embodiments, contemplated pharmaceutical formulations include an intragranular phase that includes a contemplated antisense compound or a pharmaceutically acceptable salt and a pharmaceutically acceptable filler. For example, Mongersen and a filler may be blended together, with optionally other excipients, and formed into granules. In some embodiments, the intragranular phase may be formed using wet granulation, e.g., a liquid (e.g., water) is added to the blended antisense compound and filler, and then combination is dried, milled and/or sieved to produce granules. One of skill in the art would understand that other processes may be used to achieve an intragranular phase.

In some embodiments, contemplated formulations include an extra-granular phase, which may include one or more pharmaceutically acceptable excipients, and which may be blended with the intragranular phase to form a disclosed formulation.

An anti-SMAD7 therapy formulation may include an intragranular phase that includes a filler. Exemplary fillers include, but are not limited to, cellulose, gelatin, calcium phosphate, lactose, sucrose, glucose, mannitol, sorbitol, microcrystalline cellulose, pectin, polyacrylates, dextrose, cellulose acetate, hydroxypropylmethyl cellulose, partially pregelatinized starch, calcium carbonate, and others including combinations thereof.

In some embodiments, an anti-SMAD7 therapy formulation may include an intragranular phase and/or an extra-granular phase that includes a binder, which may generally function to hold the ingredients of the pharmaceutical formulation together. Exemplary binders include invention may be, but are not limited to, the following: starches, sugars, cellulose or modified cellulose such as hydroxypropyl cellulose, lactose, pregelatinized maize starch, polyvinyl pyrrolidone, hydroxypropyl cellulose, hydroxypropylmethyl cellulose, low substituted hydroxypropyl cellulose, sodium carboxymethyl cellulose, methyl cellulose, ethyl cellulose, sugar alcohols and others including combinations thereof.

Contemplated anti-SMAD7 therapy formulations, e.g., that include an intragranular phase and/or an extragranular phase, may include a disintegrant such as but are not limited to, starch, cellulose, crosslinked polyvinyl pyrrolidone, sodium starch glycolate, sodium carboxymethyl cellulose, alginates, corn starch, crosmellose sodium, crosslinked carboxymethyl cellulose, low substituted hydroxypropyl cellulose, acacia, and others including combinations thereof. For example, an intragranular phase and/or an extragranular phase may include a disintegrant.

In some embodiments, a contemplated anti-SMAD7 therapy formulation includes an intra-granular phase comprising a disclosed antisense compound and excipients chosen from: mannitol, microcrystalline cellulose, hydroxypropylmethyl cellulose, and sodium starch glycolate or combinations thereof, and an extra-granular phase comprising one or more of: microcrystalline cellulose, sodium starch glycolate, and magnesium stearate or mixtures thereof.

In some embodiments, a contemplated anti-SMAD7 therapy formulation may include a lubricant, e.g., an extra-granular phase may contain a lubricant. Lubricants include but are not limited to talc, silica, fats, stearin, magnesium stearate, calcium phosphate, silicone dioxide, calcium silicate, calcium phosphate, colloidal silicon dioxide, metallic stearates, hydrogenated vegetable oil, corn starch, sodium benzoate, polyethylene glycols, sodium acetate, calcium stearate, sodium lauryl sulfate, sodium chloride, magnesium lauryl sulfate, talc, and stearic acid.

In some embodiments, the pharmaceutical formulation comprises an enteric coating. Generally, enteric coatings create a barrier for the oral medication that controls the location at which the drug is absorbed along the digestive tract. Enteric coatings may include a polymer that disintegrates a different rates according to pH. Enteric coatings may include for example, cellulose acetate phthalate, methyl acrylate-methacrylic acid copolymers, cellulose acetate succinate, hydroxylpropylmethyl cellulose phthalate, methyl methacrylate-methacrylic acid copolymers, ethylacrylate-methacrylic acid copolymers, methacrylic acid copolymer type C, polyvinyl acetate-phthalate, and cellulose acetate phthalate.

In some embodiments, the enteric coating includes an anionic, cationic, or neutral copolymer based on methacrylic acid, methacrylic/acrylic esters or their derivatives. In some embodiments, the enteric coating includes an ethylacrylate-methacrylic acid copolymer. Commercially available enteric coatings include Opadry® AMB, Acryl-EZE®, Eudragit® grades. In some embodiments, the enteric coating makes up about 5% to about 10%, about 5% to about 20%, about 8 to about 15%, about 8% to about 18%, about 10% to about 12%, or about 12% to about 16%, of a contemplated tablet by weight.

For example, an anti-SMAD7 therapy in the form of a tablet is provided that comprises or consists essentially of about 0.5% to about 70%, e.g., about 0.5% to about 10%, or about 1% to about 20%, by weight of an antisense oligonucleotide or a pharmaceutically acceptable salt thereof (e.g., Mongersen). Such a tablet may include for example, about 0.5% to about 60% by weight of mannitol, e.g., about 30% to about 50% by weight mannitol, e.g., about 40% by weight mannitol; and/or about 20% to about 40% by weight of microcrystalline cellulose, or about 10% to about 30% by weight of microcrystalline cellulose. For example, a contemplated tablet may comprise an intragranular phase that includes about 30% to about 60%, e.g., about 45% to about 65% by weight, or alternatively, about 5 to about 10% by weight Mongersen, about 30% to about 50%, or alternatively, about 5% to about 15% by weight mannitol, about 5% to about 15% microcrystalline cellulose, about 0% to about 4%, or about 1% to about 7% hydroxypropylmethyl cellulose, and about 0% to about 4%, e.g., about 2% to about 4% sodium starch glycolate by weight.

Exemplary anti-SMAD7 therapy formulations include dosage forms that include or consist essentially of about 10 mg to about 500 mg of Mongersen, for example, tablets that include about 10 mg, about 15 mg, about 20 mg, about 25 mg, about 30 mg, about 35 mg, about 40 mg, about 50 mg, about 60 mg, about 70 mg, about 80 mg, about 90 mg, about 100 mg, about 150 mg, about 200 mg, or about 250 mg of Mongersen are contemplated herein. In one embodiment, the anti-SMAD7 therapy may be a tablet for oral use comprising: about 0.5% to about 10% by weight of an antisense oligonucleotide represented by SEQ ID NO: 4 or a pharmaceutically acceptable salt thereof; about 30% to about 50% by weight mannitol; and about 10% to about 30% by weight microcrystalline cellulose.

In an exemplary embodiment of the invention, a pharmaceutically acceptable tablet for oral administration is provided that includes an intra-granular phase that may comprise about 50% by weight Mongersen (or salt thereof), about 11.5% by weight mannitol, about 10% by weight microcrystalline cellulose, about 3% by weight hydroxypropylmethyl cellulose, and about 2.5% by weight sodium starch glycolate; and an extra-granular phase that may comprise about 20% by weight microcrystalline cellulose, about 2.5% by weight sodium starch glycolate, and about 0.5% by weight magnesium stearate. The tablet may also include an enteric coating.

In another exemplary embodiment, a pharmaceutically acceptable tablet for oral administration is provided that includes or consists essentially of: an intra-granular phase that may comprise or consist essentially of about 5% to about 10%, e.g., about 8% by weight Mongersen (e.g., wherein the internucleotide linkages are each O,O-linked phophorothioates, and/or salt thereof, e.g., a sodium salt), about 40% by weight mannitol, about 8% by weight microcrystalline cellulose, about 5% by weight hydroxypropylmethyl cellulose, and about 2% by weight sodium starch glycolate; and an extra-granular phase that may comprise about 17% by weight microcrystalline cellulose, about 2% by weight sodium starch glycolate, and about 0.4% by weight magnesium stearate.

Contemplated tablets may also include an enteric coating, e.g., a disclosed tablet may include about 13%, about 14%, about 15%, about 16%, or about 17% by weight of an enteric coating, e.g., ethylacrylate-methacrylic acid copolymers (e.g., AcrylEZE®).

For example, the anti-SMAD7 therapy may be in the form of a pharmaceutically acceptable tablet for oral use comprising an intra-granular phase and extra-granular phase, wherein for example, the intra-granular phase comprises about 5% to about 10%, by weight (for example about 8% by weight) of an antisense oligonucleotide represented by SEQ ID NO: 4 or a pharmaceutically acceptable salt thereof, about 40% by weight mannitol, about 8% by weight microcrystalline cellulose, about 5% by weight hydroxypropylmethyl cellulose, and about 2% by weight sodium starch glycolate, and for example, the extra-granular phase comprises about 17% by weight microcrystalline cellulose, about 2% by weight sodium starch glycolate, and about 0.4% by weight magnesium stearate, where the tablet may further comprise an enteric coating.

Contemplated formulations, e.g., tablets, in some embodiments, when orally administered to the patient may result in minimal plasma concentration of the oligonucleotide in the patient. In another embodiment, contemplated formulations, when orally administered to a patient, topically deliver to the terminal ileum and/or right colon of a patient, e.g., to an affected or diseased intestinal site of a patient. Formulations suitable for oral administration may be in the form of capsules, cachets, pills, tablets, lozenges (using, e.g., a flavored basis such as sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

Inflammatory Bowel Disease

"Inflammatory bowel disease" or "IBD," as used herein, may refer to a number of chronic inflammatory diseases including Crohn's disease (CD), gastroduodenal Crohn's disease, Crohn's (granulomatous) colitis, ulcerative colitis (UC), collagenous colitis, lymphocytic colitis, ischaemic colitis, diversion colitis, Behçet's disease, microscopic colitis, ulcerative proctitis, proctosigmoiditis, jejunoileitis, left-sided colitis, pancolitis, ileocolitis, ileitis, and indeterminate colitis. CD and UC are the two most common forms of IBD. IBD is an autoimmune disease of the digestive system. CD may be localized to any portion of the gastrointestinal tract, including the terminal ileum, and may impact all cell types of the gastrointestinal tract. UC is localized to the colon and rectum, and affects cells of the mucosa only.

Intestinal Fibrosis

Figure 2:
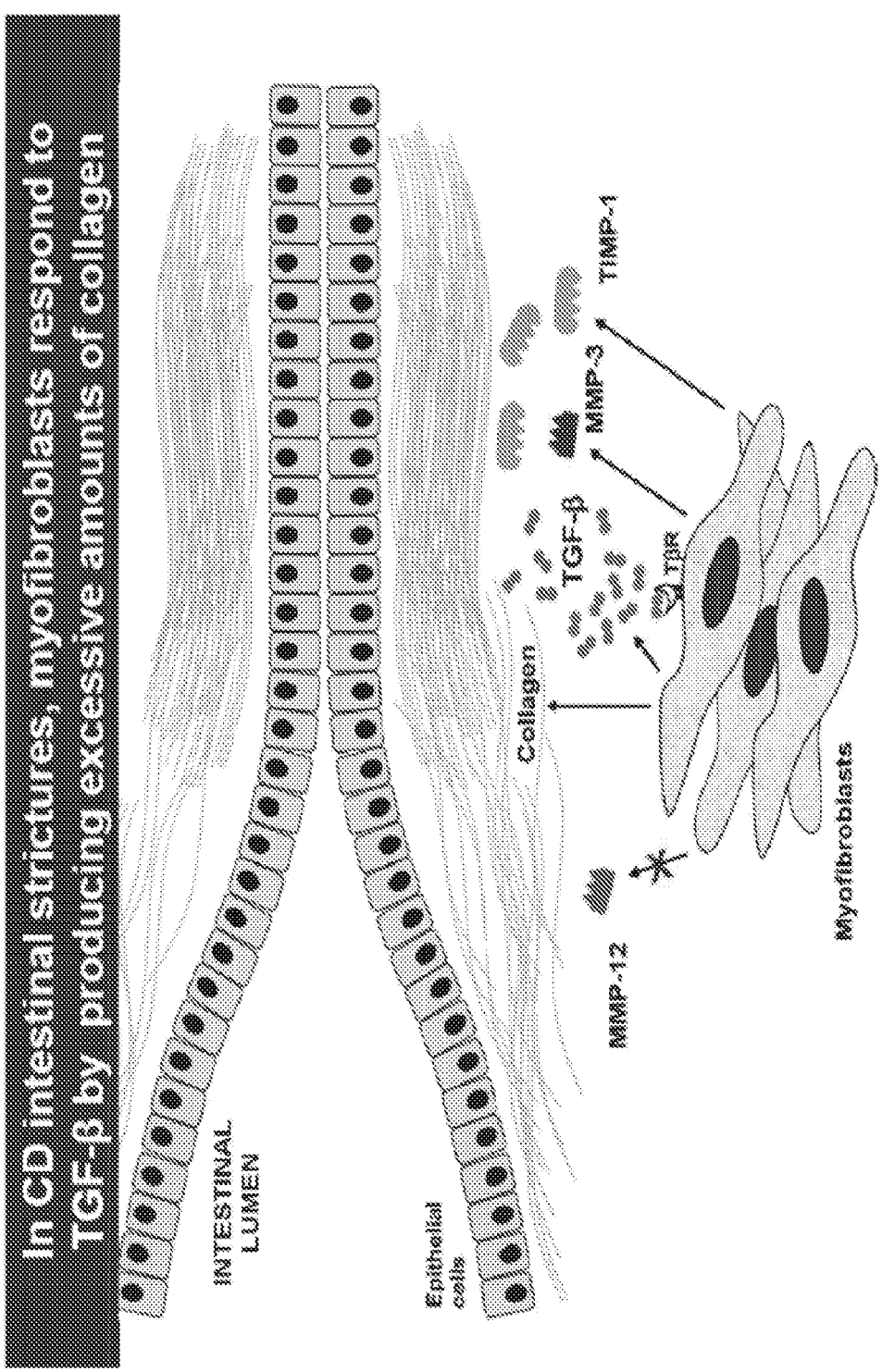
FIG. 2. In Crohn's disease intestinal strictures, myofibroblasts respond to TGF-β by producing excessive amounts of collagen.

Intestinal fibrosis commonly results from the reaction of intestinal tissue to inflammation, such as chronic inflammation caused by IBD. In IBD, increased levels of SMAD7 block anti-inflammatory gene expression mediated via TGF-β pathway activation and Smad2/3 phosphorylation (FIG. 1). Myofibroblasts exposed to increased TGF-β signaling produce increased amounts of collagen (FIG. 2). In the context of Crohn's disease, persistent and chronic inflammation promotes fibrotic processes, resulting in the formation of strictures, including small bowel and colonic strictures.

Intestinal fibrosis can be identified by any of a number of imaging techniques, such as contrast-enhanced ultrasonography. See, e.g., Quaia et al. The value of small bowel wall contrast enhancement after sulfur hexafluoride-filled microbubble injection to differentiate inflammatory from fibrotic strictures in patients with Crohn's disease. *Ultrasound Med. Biol.* 38, 1324-1332 (2012); Nylund et al. Quantitative contrast-enhanced ultrasound comparison between inflammatory and fibrotic lesions in patients with Crohn's disease. *Ultrasound Med. Biol.* 39, 1197-1206 (2013); Stidham et al. Ultrasound elasticity imaging for detecting intestinal fibrosis and inflammation in rats and humans with Crohn's disease. *Gastroenterology* 141, 819-826 (2011). MRI techniques such as magnetization transfer MRI can also be used. See, e.g., Maccioni et al. Value of T2-weighted magnetic resonance imaging in the assessment of wall inflammation and fibrosis in Crohn's disease. *Abdom. Imaging* 37, 944-957 (2012); Adler et al. Magnetization transfer helps detect intestinal fibrosis in an animal model of Crohn disease. *Radiology* 259, 127-135 (2011); Pazahr et al. Magnetization transfer for the assessment of bowel fibrosis in patients with Crohn's disease: initial experience. *Magn. Reson. Mat. Phys. Biol. Med.* 26, 291-301 (2013).

Treatment and Management

A "patient," as described herein, refers to any animal suffering from or diagnosed for intestinal fibrosis, including, but not limited to, mammals, primates, and humans. In certain embodiments, the subject may be a non-human mammal such as, for example, a cat, a dog, or a horse. In a preferred embodiment, the subject is a human subject.

The terms "treat," "treatment," "treating," and the like are used herein to generally mean obtaining a desired pharmacological and/or physiological effect. The effect may be therapeutic in terms of partially or completely curing a disease and/or adverse effect attributed to the disease. The term "treatment" as used herein covers any treatment of a disease in a mammal, particularly a human, and includes: (a) inhibiting the disease, i.e., preventing the disease from increasing in severity or scope; (b) relieving the disease, i.e., causing partial or complete amelioration of the disease; or (c) preventing relapse of the disease, i.e., preventing the disease from returning to an active state following previous successful treatment of symptoms of the disease or treatment of the disease.

The terms "manage," "management," "managing," and the like are used herein to generally mean controlling the severity or manifestation of symptoms of a disease, or the means of treating the disease. Generally, management is used to obtaining a desired pharmacological and/or physiological effect. The effect may be therapeutic in terms of partially or completely curing a disease and/or adverse effect attributed to the disease or ensuring that a particular symptom or manifestation of the disease does not occur or reoccur in a patient or does not rise to an undesirable or intolerable level in a patient. The term "management" as used herein covers any management of a disease in a mammal, particularly a human, and includes: (a) inhibiting the disease, i.e., preventing the disease from increasing in severity or scope; (b) relieving the disease, i.e., causing partial or complete amelioration of the disease; or (c) preventing relapse of the disease, i.e., preventing the disease from returning to an active state following previous successful treatment of symptoms of the disease or treatment of the disease. "Management" as used herein may also be used with reference to administration of a specific treatment for the disease, for example, a SMAD7 antisense oligonucleotide.

In some embodiments of the invention, a patient having intestinal fibrosis will be administered an initial dose of an anti-SMAD7 therapy, for instance, an anti-SMAD7 oligonucleotide (e.g., a SMAD7 antisense oligonucleotide, SMAD7 RNAi or SMAD7 miRNA). As used herein, "initial dose" refers to a dose of an anti-SMAD7 therapy administered to a patient having intestinal fibrosis, in a series of doses. A series of doses may include one or more doses. For instance, a series of doses may comprise a single dose of an anti-SMAD7 therapy or more than a single dose of an anti-SMAD7 therapy. An initial dose may be a dose of an anti-SMAD7 therapy administered to a patient prior to any later dose administered to the patient. For instance, an initial dose may be, but is not limited to, the first dose of an anti-SMAD7 therapy administered to a treatment-naïve patient. An initial dose may also be a first dose in any treatment cycle of the anti-SMAD7 therapy. For example, an initial dose may be the first dose of a first treatment cycle, of a second treatment cycle, or of any subsequent treatment cycles. Alternatively, an "initial dose" may be the first dose administered to a patient after analyzing levels of p-SMAD3, α-SMA, or TGF-β and/or another biomarker or biomarkers in a patient, or may be the most recently administered dose before a determination of the levels of p-SMAD3, α-SMA, or TGF-β and/or another biomarker or biomarkers in a patient.

In some embodiments of the invention, a patient having intestinal fibrosis will be administered a subsequent dose of an anti-SMAD7 therapy, for instance, an anti-SMAD7 oligonucleotide (e.g., a SMAD7 antisense oligonucleotide, SMAD7 RNAi or SMAD7 miRNA). As used herein, "subsequent dose" refers to a dose of an anti-SMAD7 therapy administered to a patient having intestinal fibrosis, after administration of a prior dose, for example, an initial dose. Thus, a subsequent dose may be administered to a patient having intestinal fibrosis in a series of doses comprising two or more doses. Furthermore, in some instances, the amount of a subsequent dose may be calibrated with respect to an initial dose or a prior dose, such that a subsequence dose is greater, equal to, or lesser than a prior dose. Calibration of the amount of a subsequent dose may be based on levels or changes in levels of p-SMAD3, α-SMA, or TGF-β and/or another biomarker or biomarkers in a patient having intestinal fibrosis, for instance: levels of p-SMAD3, α-SMA, or TGF-β in a patient having intestinal fibrosis analyzed prior to or after a prior dose, for instance, an initial dose; or changes in p-SMAD3, α-SMA, or TGF-β levels in a patient having intestinal fibrosis before and after a prior dose, for instance, an initial dose. A subsequent dose may be a dose administered to a patient having intestinal fibrosis after a first dose, for instance, an initial dose, of an anti-SMAD7 therapy administered to a patient having intestinal fibrosis. A subsequent dose may also be a dose administered after a prior dose of an anti-SMAD7 therapy administered to a patient having intestinal fibrosis, for instance, a dose administered after a prior dose in the same round of treatment or a different round of treatment, for instance, a previous round of treatment. A subsequent dose may be a subsequent dose with respect to any prior dose, for instance, a prior dose immediately preceding the subsequent dose or a prior dose followed by one or more doses administered prior to administration of the subsequent dose.

Patients treated using an above method may or may not have detectable fibrosis. In some embodiments, the patient has at least about a 5%, 10%, 20%, 30%, 40% or even 50% or more reduction in the amount of fibrosis present in the patient after administering a specific inhibitor of SMAD7, after e.g., 1 day, 2 days, 1 week, 1 month, or 6 months, or more. Administering an inhibitor of SMAD7 may be on, e.g., at least a daily basis. The delay of clinical manifestation of fibrosis in a patient as a consequence of administering an inhibitor of SMAD7 may be at least e.g., 6 months, 1 year, 18 months or even 2 years or more as compared to a patient who is not administered an inhibitor of SMAD7.

A patient at risk of intestinal fibrosis may include those patients with ulcerative colitis, inflammatory bowel disease, or Crohn's disease. A patient at risk may also include those patients with an early age at diagnosis of Crohn's or colitis, extensive and/or severe of colonic disease, patients with the presence of primary sclerosing cholangitis, and/or patient's having a family history of cancer.

As used herein, "SMAD7" (also known as CRCS3, FLJ16482, MADH7, MADH8, MAD (mothers against decapentaplegic, Drosophila) homolog 7, MAD homolog 8, SMAD, mothers against DPP homolog 7, mothers against DPP homolog 8) means the human protein or any of the mRNA transcripts encoded by the gene identified by Entrez GeneID No. 4092 and allelic variants thereof.

As used herein, "TGF-β" (also known as CED; LAP; DPD1; TGFB; and TGFbeta) means the human protein or any of the mRNA transcripts encoded by the gene identified by Entrez GeneID No. 7040 and allelic variants thereof.

As used herein, "α-SMA" (also known as ACTA; ASMA; CFTD; MPFD; NEM1; NEM2; NEM3; CFTD1; and CFTDM) means the human protein or any of the mRNA transcripts encoded by the gene identified by Entrez GeneID No. 58 and allelic variants thereof.

As used herein, "SMAD3" (also known as LDS3; LDS1C; MADH3; JV15-2; HSPC193; and HsT17436) means the human protein or any of the mRNA transcripts encoded by the gene identified by Entrez GeneID No. 4088 and allelic variants thereof.

As used herein, "anti-SMAD7 oligonucleotide" refers to an oligonucleotide comprising a nucleic acid sequence that is complementary to a nucleic acid sequence in the coding region of SMAD7. In some embodiments, the anti-SMAD7 oligonucleotide comprises a SMAD7 antisense oligonucleotide, SMAD7 RNAi, or SMAD7 miRNA. In some embodiments, the anti-SMAD7 oligonucleotide can reduce the expression of a gene that comprises a complementary nucleic acid sequence when the anti-SMAD7 oligonucleotide is introduced into a cell (e.g., an immune cell, such as PBMC, pDC, or B-cell). In some embodiments, the anti-SMAD7 oligonucleotide can reduce expression of an mRNA transcribed from the gene. In some embodiments, the anti-SMAD7 oligonucleotide can reduce expression of a protein encoded by the gene. In some embodiments, the anti-SMAD7 oligonucleotide can reduce secretion of a protein encoded by the gene from the cell into which the anti-SMAD7 oligonucleotide was introduced.

As used herein, a "SMAD7 antisense oligonucleotide" is an oligonucleotide comprising a nucleic acid sequence that is complementary to the nucleic acid sequence of a SMAD7 mRNA, SMAD7 cDNA, or the coding strand of a SMAD7 DNA.

Methods of Monitoring Treatment

In some embodiments, the methods described herein entail monitoring the treatment, disease state, or biomarkers associated with a disease state of a patient having intestinal fibrosis. Monitoring treatment may be useful in terms of assessing treatment efficacy and safety, as well as evaluating the need to modulate treatment. Monitoring treatment may also be useful for evaluating whether the amount of SMAD7 antisense oligonucleotide being administered to a patient or which will be administered to a patient should be increased or decreased. Furthermore, monitoring treatment may be useful in terms of determining the amount or relative amount by which a dose of SMAD7 antisense oligonucleotide should be modulated, i.e., increased or decreased.

Monitoring, for example, monitoring of p-SMAD3, α-SMA, or TGF-β levels in a patient having intestinal fibrosis, may commence prior to, during, or after an initial dose of a SMAD7 antisense oligonucleotide. Furthermore, monitoring may continue after an initial dose. For example monitoring may be performed after administration of an initial dose. Monitoring may also be performed before, during, or after a subsequent dose of SMAD7 antisense oligonucleotide. Monitoring may be continuous or discontinuous such that monitoring may be performed at regular intervals, for example, after each dose of a SMAD7 antisense oligonucleotide is administered to a patient, before each dose of a SMAD7 antisense oligonucleotide is administered to a patient, or before and after each dose of a SMAD7 antisense oligonucleotide is administered to a patient. Monitoring may be performed multiple times in a single day (for instance, 2 times, 3 times, 4 times, about five times, or about 10 times in a single day), once a day, multiple times in a single week (for instance, 2 times, 3 times, 4 times, about five times, or about 10 times in a single week), once a week, multiple times in a single month (for instance, 2 times, 3 times, 4 times, about five times, or about 10 times in a single month), or once a month. In methods of the invention, monitoring may be performed at various times relative to an administering step. For instance, in some embodiments, monitoring may be performed immediately after, or at least 1 day, at least 3 days, at least 5 days, at least 1 week, at least 2 weeks, at least 3 weeks, at least 1 month, at least 2 months, at least 4 months, or at least 6 months after an administration step. In some embodiments, monitoring is performed about 15 days or about 28 days after an administration step.

As described above, the invention is based in part on the discovery that levels of p-SMAD3, α-SMA, or TGF-β can be used to evaluate and modify management and treatment with a SMAD7 antisense oligonucleotide in a patient having intestinal fibrosis. Thus, in embodiments of the invention, it is useful to know, determine, analyze, or compare levels of p-SMAD3, α-SMA, or TGF-β in a patient or a sample from a patient having intestinal fibrosis. For example, in some instances it will be useful to know a threshold value for normal or abnormal levels of p-SMAD3, α-SMA, or TGF-β in order to determine whether levels of the SMAD7 antisense oligonucleotide should be increased, decreased, or left untouched. In the methods described herein, a normal level of p-SMAD3, α-SMA, or TGF-β may be tied to a specific value, for instance, a value of 0.01 pg/ml, about 0.1 pg/ml, about 1 pg/ml, about 2 pg/ml, about 3 pg/ml, about 4 pg/ml, about 5 pg/ml, about 6 pg/ml, about 7 pg/ml, about 8 pg/ml, about 9 pg/ml, about 10 pg/ml, about 11 pg/ml, about 12 pg/ml, about 13 pg/ml, about 14 pg/ml, about 15 pg/ml, about 17.5 pg/ml, about 20 pg/ml, about 22.5 pg/ml, about 25 pg/ml, about 30 pg/ml, or about 35 pg/ml, about 12.5 pg/ml, about 16 pg/ml, about 17 pg/ml, about 18 pg/ml, about 19 pg/ml, about 40 pg/ml, about 50 pg/ml, about 60 pg/ml, about 70 pg/ml, about 80 pg/ml, about 90 pg/ml, or about 100 pg/ml. In some embodiments, a normal level of p-SMAD3, α-SMA, or TGF-β may be determined by comparison to median levels of p-SMAD3, α-SMA, or TGF-β in a healthy control group that is matched to the patient with respect to various factors, for example, age, gender, ethnic origin, smoking habits, dietary habits, body-mass index (BMI), and/or exercise habits.

Levels of p-SMAD3, α-SMA, TGF-β and/or other analytes may be determined by obtaining a sample from the patient. According to the methods described herein, a sample may be a tissue sample (e.g., an intestinal tissue sample) or a bodily fluid sample (e.g., a saliva sample, a stool, or a urine sample). A sample can be a sample obtained from a patient tissue biopsy, for example, a mucosal tissue biopsy, for example, an intestinal mucosal tissue biopsy. Furthermore, the sample may be a blood, serum, or plasma sample. A blood sample from a subject may be obtained using techniques well-known in the art. Blood samples may include peripheral blood mononuclear cells (PMBCs), RBC-depleted whole blood, or blood serum. PBMCs can be separated from whole blood samples using different density gradient (e.g., Ficoll density gradient) centrifugation procedures. For example, whole blood (e.g., anticoagulated whole blood) is layered over the separating medium and centrifuged. At the end of the centrifugation step, the following layers are visually observed from top to bottom: plasma/platelets, PBMC, separating medium and erythrocytes/granulocytes.

Methods of monitoring treatment may also include methods of monitoring other factors, including, but not limited to levels of other analytes (e.g., p-SMAD3, α-SMA, TGF-β, Collagens I-III, CTGF, PDGF, IL-13) and presence or severity of intestinal fibrosis symptoms.

In embodiments of the invention where levels of an analyte (e.g., p-SMAD3, α-SMA, or TGF-β) are measured, various methods may be used to measure the analyte. For example, the level of an analyte, for example, p-SMAD3, α-SMA, or TGF-β, may be determined by immunochemistry and/or by nucleotide analysis. Methods of determining analyte concentration by immunochemistry include, but are not limited to, Western blotting, ELISA, and immunostaining methods. In some embodiments, a method of determining analyte concentration by immunochemistry is performed using an antibody that can bind to the analyte of interest, for instance, an anti-p-SMAD3 antibody, an anti-α-SMA antibody, or an anti-TGF-β antibody. Methods of determining analyte concentration by immunochemistry may also involve the use of buffers, blocking reagents, unconjugated primary antibodies, and primary and/or secondary antibodies conjugated to tags that allow for antibody detection, such as fluorescent probes or substrate-specific enzymes.

Methods of determining analyte concentration by nucleotide analysis include, but are not limited to, methods of analyzing analyte mRNA transcript levels such as Northern blotting and polymerase chain reaction methods, for example, quantitative polymerase chain reaction methods. Nucleotide analysis may be performed using an oligonucleotide probe that binds an analyte nucleotide sequence (e.g., a p-SMAD3, α-SMA, or TGF-β nucleotide sequence) or a pair of oligonucleotide primers capable of amplifying an analyte nucleotide sequence via a polymerase chain reaction, for example, by a quantitative polymerase chain reaction. Oligonucleotide probes and oligonucleotide primers may be linked to a detectable tag, such as, for example, a fluorescent tag. In determining analyte concentration by nucleotide analysis, the practitioner may evaluate a particular analyte's mRNA transcript concentration in a sample. Alternatively, in determining analyte concentration by nucleotide analysis, the practitioner may establish a correlation between a particular analyte's mRNA transcript abundance and the particular analyte's protein abundance in order to extrapolate analyte protein concentration based on a measure of analyte mRNA transcript abundance.

Methods of the claimed invention include steps that may be carried out in vitro. For instance, it is contemplated that the steps of measuring p-SMAD3, α-SMA, or TGF-β levels in the subject, determining the levels of p-SMAD3, α-SMA, or TGF-β in a sample. For example, the level of p-SMAD3, α-SMA, or TGF-β in a sample may be determined by performing immunochemistry or nucleotide analysis on the sample in vitro. Alternatively, in some embodiments of the invention, the steps of determining and analyzing the p-SMAD3, α-SMA, or TGF-β levels in a patient having intestinal fibrosis or determining and analyzing the p-SMAD3, α-SMA, or TGF-β levels in a sample may be carried out in vivo.

Enzyme-Linked Immunosorbent Assay

In some embodiments, p-SMAD3, α-SMA, or TGF-β and/or other analyte concentration may be determined by Enzyme-linked immunosorbent assay (ELISA). Specifically, levels of p-SMAD3, α-SMA, or TGF-β and/or other analytes in a sample, especially a blood sample, for example, a blood serum sample, can be determined by ELISA. Assaying analyte concentration by ELISA requires at least one antibody against the analyte protein, e.g., at least one anti-p-SMAD3 antibody, anti-TGF-β antibody, or anti-α-SMA antibody, and/or at least one secondary antibody, e.g., at least one labeled secondary antibody. In some embodiments, the primary antibody is labeled with, e.g., a fluorescent label. In certain embodiments, the primary antibody is not labeled and a secondary antibody capable of binding the species isotype of the primary antibody is labeled, e.g., with a fluorescent probe or enzyme capable of reacting with a specific substrate, thereby providing a detectable signal.

Performing an ELISA requires at least one capture antibody, at least one detection antibody, and/or at least one enzyme-linked or fluorescent labeled secondary antibody. For example, assaying p-SMAD3, α-SMA, or TGF-β levels by ELISA may require an anti-p-SMAD3 antibody, anti-α-SMA antibody, or anti-TGF-β antibody, respectively, as the capture antibody. The anti-p-SMAD3 antibody, anti-α-SMA antibody, or anti-TGF-β antibody is immobilized on a solid support such as a polystyrene microtiter plate. A sample, for example, a blood serum sample is then added and allowed to complex with the bound antibody. Unbound serum components are removed with a wash. A detection antibody, e.g., a different anti-p-SMAD3 antibody, anti-α-SMA antibody, or anti-TGF-β antibody, e.g., an anti-p-SMAD3 antibody, anti-α-SMA antibody, or anti-TGF-β antibody, that binds to a different portion of the p-SMAD3, α-SMA, or TGF-β protein, respectively, than the capture antibody, is added and is allowed to bind to the captured p-SMAD3, α-SMA, or TGF-β. The detection antibody is linked to a detectable tag, such as an enzyme, either directly or indirectly, e.g., through a secondary antibody that specifically recognizes the detection antibody. Typically between each step, the plate, with bound protein, is washed with a wash buffer, e.g., a mild detergent solution. Typical ELISA protocols also include one or more blocking steps, which involve use of a non-specifically-binding protein such as bovine serum albumin to block unwanted non-specific binding of protein reagents to the plate. After a final wash step, the plate is developed by addition of an appropriate enzyme substrate, to produce a visible signal, which indicates the amount of p-SMAD3, α-SMA, or TGF-β protein in the sample. The substrate can be, e.g., a chromogenic substrate or a fluorogenic substrate. ELISA methods, reagents and equipment are well-known in the art and commercially available.

Nucleotide Analysis

In some embodiments, levels of p-SMAD3, α-SMA, or TGF-β and/or other analytes may be determined by performing a "nucleotide analysis." A nucleotide analysis may include analysis of analyte nucleotide transcript levels (e.g., p-SMAD3, α-SMA, or TGF-β mRNA transcript levels) in a sample, for example, a blood sample. Analyte transcript levels may be determined by Northern blot, for example, a quantitative Northern blot; or polymerase chain reaction, for example, a quantitative polymerase chain reaction. Reagents necessary to perform Northern blot include oligonucleotide probes, for example, oligonucleotide probes linked to a detectable label. Detectable labels may include fluorescent labels or enzymes capable of reacting with a specific substrate. Reagents necessary to perform polymerase chain reaction include oligonucleotide primers capable of specifically binding to a particular analyte mRNA transcript and amplifying the number of analyte mRNA transcripts by polymerase chain reaction. Oligonucleotide primers may be linked to a detectable label to enable, for example, quantitative polymerase chain reaction. Other reagents necessary to perform quantitative polymerase chain reaction include, but are not limited to, primers capable of amplifying a control transcript signal, for instance, a beta tubulin transcript signal. Buffers, reagents (including oligonucleotide primers and probes), techniques, and equipment necessary for performing Northern blotting and polymerase chain reactions are readily available and are well-known in the art.

Methods of Selecting Patients

The invention described herein provides methods of treating, preventing or managing patients in part by selecting patients that show some likelihood of responsiveness to SMAD7-antisense oligonucleotide therapy. Likeliness of responsiveness to anti-SMAD7 therapy is premised in part on determining levels of p-SMAD3, α-SMA, or TGF-β in a patient with intestinal fibrosis, for example, preexisting levels of p-SMAD3, α-SMA, or TGF-β (i.e., levels of p-SMAD3, α-SMA, or TGF-β in a patient prior to administration of an initial dose of a SMAD7 antisense oligonucleotide) or levels of p-SMAD3, α-SMA, or TGF-β determined after an initial dose or one or more subsequent doses of SMAD7 antisense oligonucleotide. For instance, in some embodiments of the invention, a patient will be selected for treatment or further treatment with a SMAD7 antisense oligonucleotide after detecting or analyzing absolute or relative p-SMAD3, α-SMA, or TGF-β levels or changes in p-SMAD3, α-SMA, or TGF-β levels. Levels of p-SMAD3, α-SMA, or TGF-β in a patient with intestinal fibrosis may be compared to a normal level of p-SMAD3, α-SMA, or TGF-β, for example, normal levels of p-SMAD3, α-SMA, or TGF-β as defined by median p-SMAD3, α-SMA, or TGF-β levels in a matched control group or absolute levels of p-SMAD3, α-SMA, or TGF-β.

In some embodiments, a patient will be selected for treatment or further treatment with a SMAD7 antisense oligonucleotide if the levels of p-SMAD3, α-SMA, or TGF-β in the patient are more than 10%, 20%, 30%, 40%, 50%, 60%, 70%, 80%, 90%, or 100% elevated relative to the average, median or mean levels of p-SMAD3, α-SMA, or TGF-β in a matched control group.

In some embodiments, a patient will be selected for treatment or further treatment with a SMAD7 antisense oligonucleotide if the level of p-SMAD3, α-SMA, or TGF-β in the patient are more than 2-fold, more than 3-fold, more than 4-fold, more than 5-fold, more than 6-fold, more than 7-fold, more than 8-fold, more than 9-fold or more than 10-fold elevated relative to the average, median or mean levels of p-SMAD3, α-SMA, or TGF-β in a matched control group.

Typically p-SMAD3, α-SMA, or TGF-β levels will be measured in terms of a concentration, for instance, mass of p-SMAD3, α-SMA, or TGF-β protein, peptide, or RNA per volume of sample, for example, volume of blood or tissue. Thus selection of patients for initial or continued treatment is tied to p-SMAD3, α-SMA, or TGF-β levels in the patient, such that, for example, high initial levels of p-SMAD3, α-SMA, or TGF-β may indicate a potential for responsiveness to SMAD7 antisense oligonucleotide treatment. Furthermore, high levels of p-SMAD3, α-SMA, or TGF-β (i.e., above normal levels of p-SMAD3, α-SMA, or TGF-β) may indicate a need for increased doses of SMAD7 antisense oligonucleotide, whereas normal or below normal levels of p-SMAD3, α-SMA, or TGF-β may indicate a need for decreased or unchanged doses of SMAD7 antisense oligonucleotide, especially following one or more doses. Alternatively, continued above normal levels of p-SMAD3, α-SMA, or TGF-β after repeated doses may indicate that the patient is not responsive to treatment.

Thus, if levels of p-SMAD3, α-SMA, or TGF-β are above normal levels of p-SMAD3, α-SMA, or TGF-β, a patient may be administered an initial and/or subsequent dose of SMAD7 antisense oligonucleotide. In some embodiments, p-SMAD3, α-SMA, or TGF-β levels are already known to be above normal p-SMAD3, α-SMA, or TGF-β levels prior to administration of an initial dose. In some embodiments, p-SMAD3, α-SMA, or TGF-β levels in a patient with intestinal fibrosis will be determined prior to administration of an initial dose. In some embodiments, after an initial dose of SMAD7 antisense oligonucleotide, if p-SMAD3, α-SMA, or TGF-β levels are analyzed and determined to be above normal levels of p-SMAD3, α-SMA, or TGF-β, the patient will be administered a subsequent dose of SMAD7 antisense oligonucleotide, for instance a greater dose than the initial dose or a dose equal to the initial dose. Alternatively, if p-SMAD3, α-SMA, or TGF-β levels are analyzed and determined to be below normal levels of p-SMAD3, α-SMA, or TGF-β, the patient may be administered a subsequent dose of SMAD7 antisense oligonucleotide, for instance an equal or smaller dose than the initial dose.

In yet other embodiments, p-SMAD3, α-SMA, or TGF-β levels may be analyzed and determined in a patient with intestinal fibrosis, and then an initial dose of SMAD7 antisense oligonucleotide may be administered to the patient if the p-SMAD3, α-SMA, or TGF-β levels are above normal levels of p-SMAD3, α-SMA, or TGF-β. Furthermore, in some embodiments, after an initial dose of SMAD7 antisense oligonucleotide, levels of p-SMAD3, α-SMA, or TGF-β may be determined, and if the levels of p-SMAD3, α-SMA, or TGF-β are above normal levels of p-SMAD3, α-SMA, or TGF-β then a subsequent dose of SMAD7 antisense oligonucleotide that is greater than or equal to the initial dose may be administered to the patient. Alternatively, after an initial dose of SMAD7 antisense oligonucleotide, levels of p-SMAD3, α-SMA, or TGF-β may be determined, and if the levels of p-SMAD3, α-SMA, or TGF-β are below normal levels of p-SMAD3, α-SMA, or TGF-β then a subsequent dose of SMAD7 antisense oligonucleotide that is smaller than or equal to the initial dose may be administered to the patient.

In yet other embodiments, the invention provides methods whereby: p-SMAD3, α-SMA, or TGF-β levels may be analyzed and determined in a patient with intestinal fibrosis; an initial dose of SMAD7 antisense oligonucleotide may be administered to the patient if the p-SMAD3, α-SMA, or TGF-β levels are above normal levels of p-SMAD3, α-SMA, or TGF-β; the levels of p-SMAD3, α-SMA, or TGF-β are analyzed after the initial administration; and if the level of p-SMAD3, α-SMA, or TGF-β after the initial dose is administered is lower than the level of p-SMAD3, α-SMA, or TGF-β before the initial dose is administered, then the patient is administered a subsequent dose that is the same as the initial dose or smaller than the initial dose. Alternatively, if the level of p-SMAD3, α-SMA, or TGF-β is unchanged or increased after the initial dose is administered compared to the level of p-SMAD3, α-SMA, or TGF-β before the initial dose is administered, then the patient is administered a subsequent dose that is the same as the initial dose or greater than the initial dose or treatment is terminated.

Thus, the contemplated invention provides different methods for treating, preventing or managing intestinal fibrosis in a patient by accounting for multiple treatment scenarios based on analysis and determination of p-SMAD3, α-SMA, or TGF-β levels and patient responsiveness to SMAD7 antisense oligonucleotide administration.

For instance, if after administration of a SMAD7 antisense oligonucleotide p-SMAD3, α-SMA, or TGF-β levels in a patient are above normal p-SMAD3, α-SMA, or TGF-β levels, treatment can continue at the same dose or at an increased dose of the SMAD7 antisense oligonucleotide.

If after administration of a SMAD7 antisense oligonucleotide p-SMAD3, α-SMA, or TGF-β levels in a patient are below normal p-SMAD3, α-SMA, or TGF-β levels, treatment can continue at the same dose or at a decreased dose of the SMAD7 antisense oligonucleotide.

If after an initial dose and one or more subsequent doses of a SMAD7 antisense oligonucleotide p-SMAD3, α-SMA, or TGF-β levels continue to be above or below normal p-SMAD3, α-SMA, or TGF-β levels, the treatment may be terminated. For example, treatment may be terminated because the patient is not responsive to treatment or the patient has been administered the maximum tolerated dose.

In some instances, if p-SMAD3, α-SMA, or TGF-β levels decrease in a patient following one or more doses of the SMAD7 antisense oligonucleotide, this may indicate that a patient is responsive to treatment. In these patients, subsequent doses of the SMAD7 antisense oligonucleotide may be administered but at the same dose or a smaller dose compared to the previous dose(s).

In some instances, if p-SMAD3, α-SMA, or TGF-β levels are stable or increase following an initial or one or more subsequent doses of the SMAD7 antisense oligonucleotide, this may indicate that a patient is not responsive to treatment. In these patients, subsequent doses of the SMAD7 antisense oligonucleotide may be administered but at a greater dose compared to the previous dose(s). Alternatively, the treatment can be discontinued, for example, if the dose approaches the maximum tolerated dose.

EXAMPLE

The invention is further illustrated by the following example. The example is provided for illustrative purposes only, and is not to be construed as limiting the scope or content of the invention in any way.

Example 1

Intestinal Fibrosis Study

Figure 3:
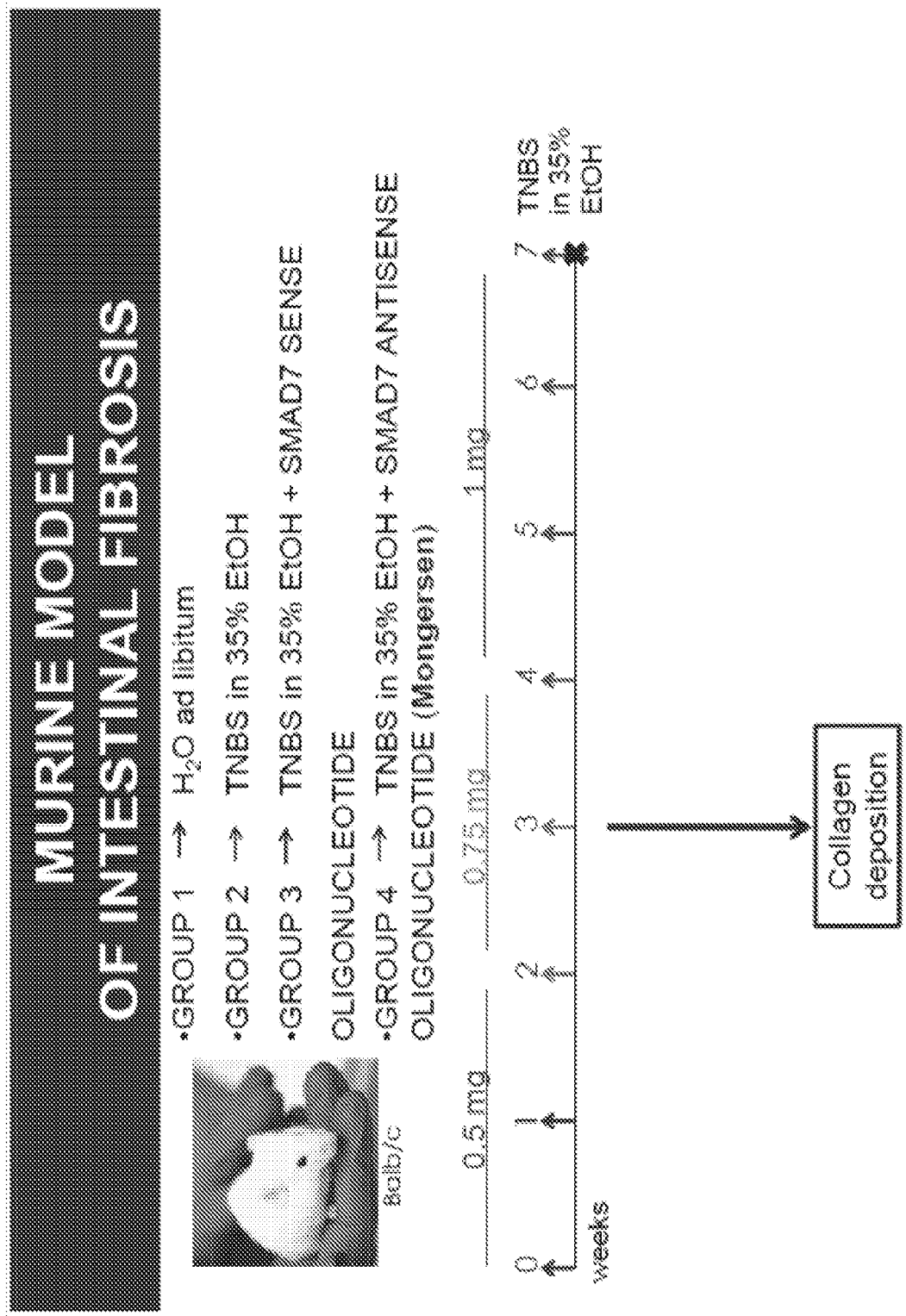
FIG. 3. Murine model of intestinal fibrosis induced by administration of trinitrobenzene sulfonic acid (TNBS). Collagen deposition is observed at week 3.
Figure 8:
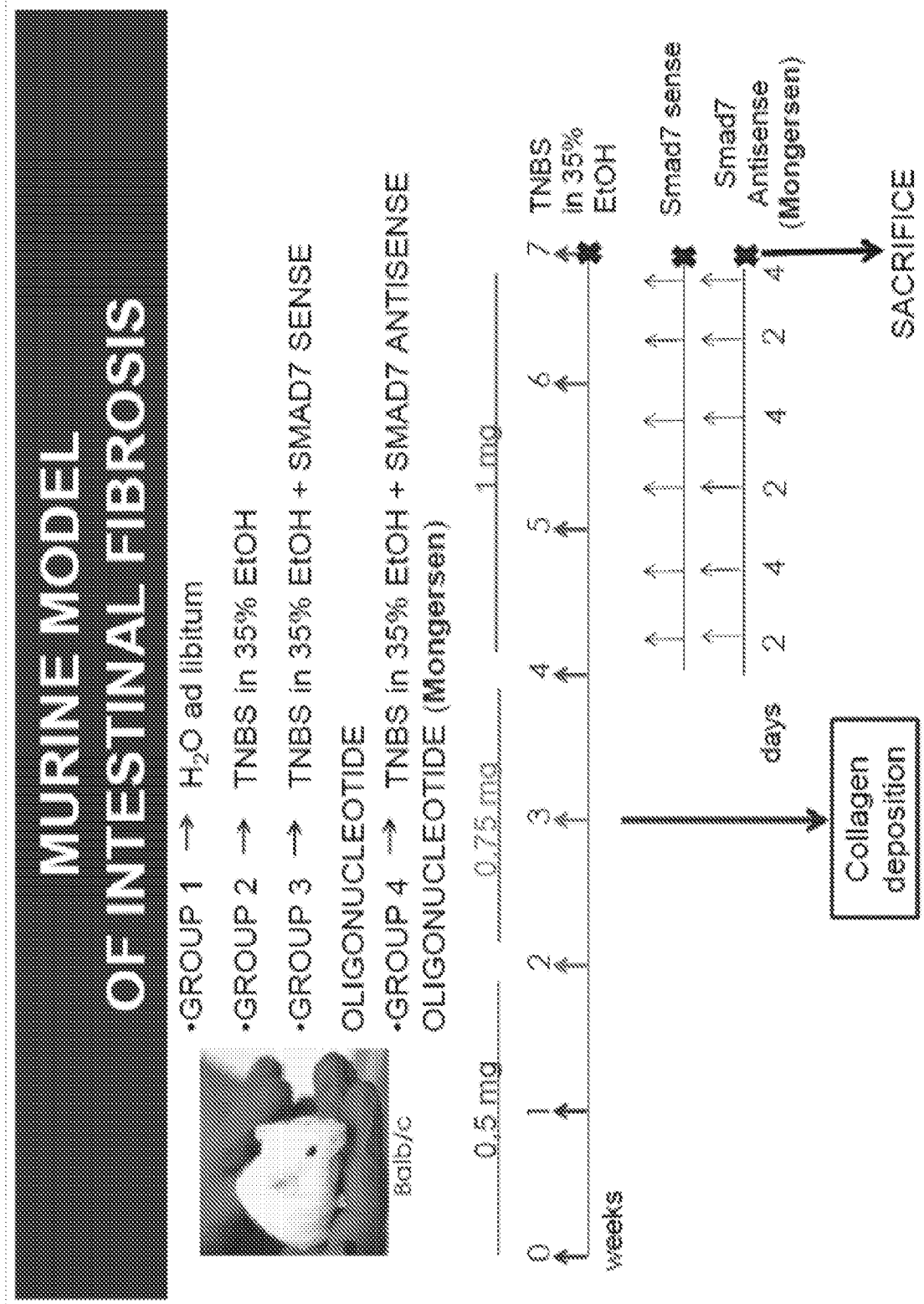
FIG. 8. Induction of intestinal fibrosis by administration of trinitrobenzene sulfonic acid (TNBS) followed by treatment with Smad7 sense oligonucleotides and Smad7 antisense oligonucleotides.
Figure 9A:
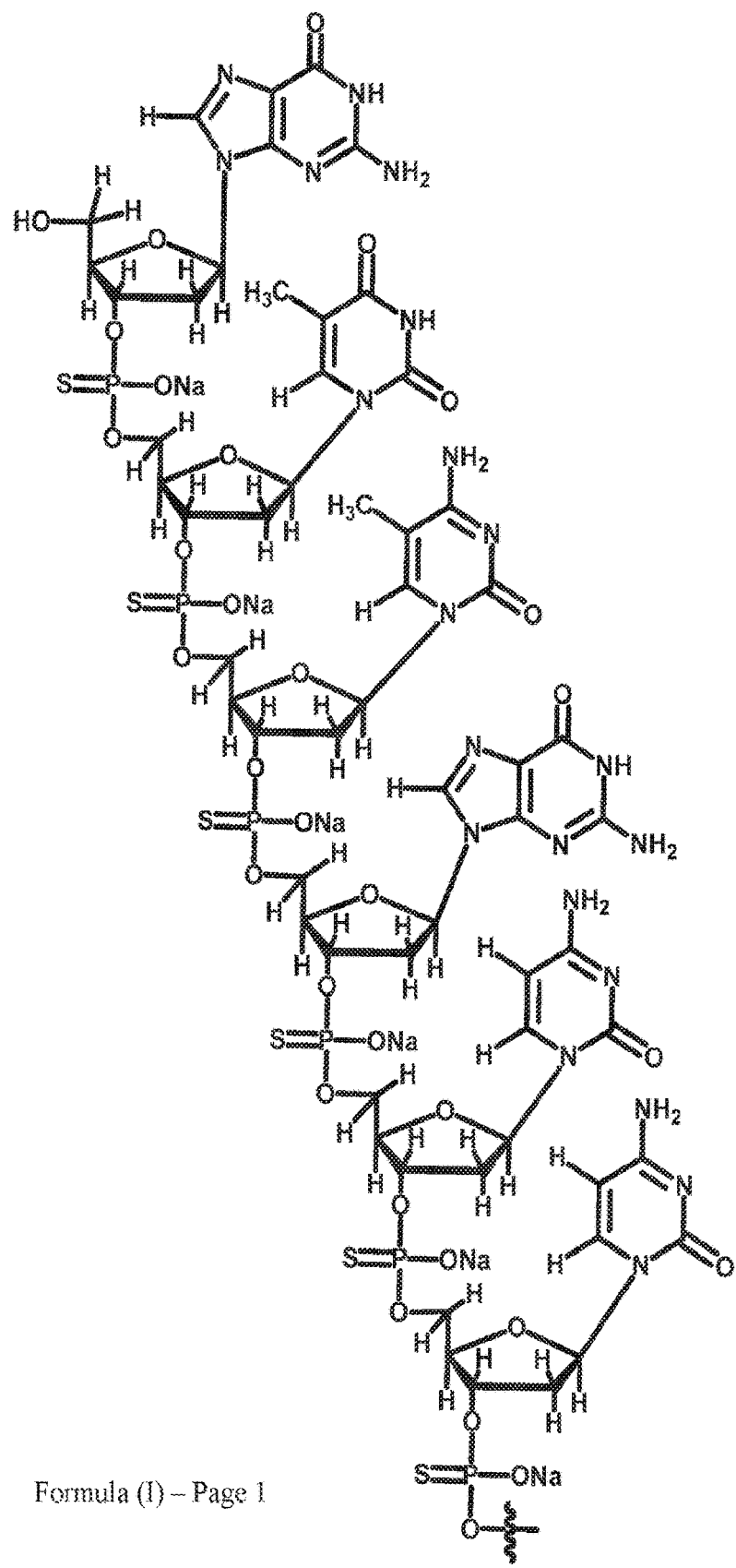
FIG. 9. Structure of Smad7 antisense oligonucleotide (Mongersen).
Figure 9B:
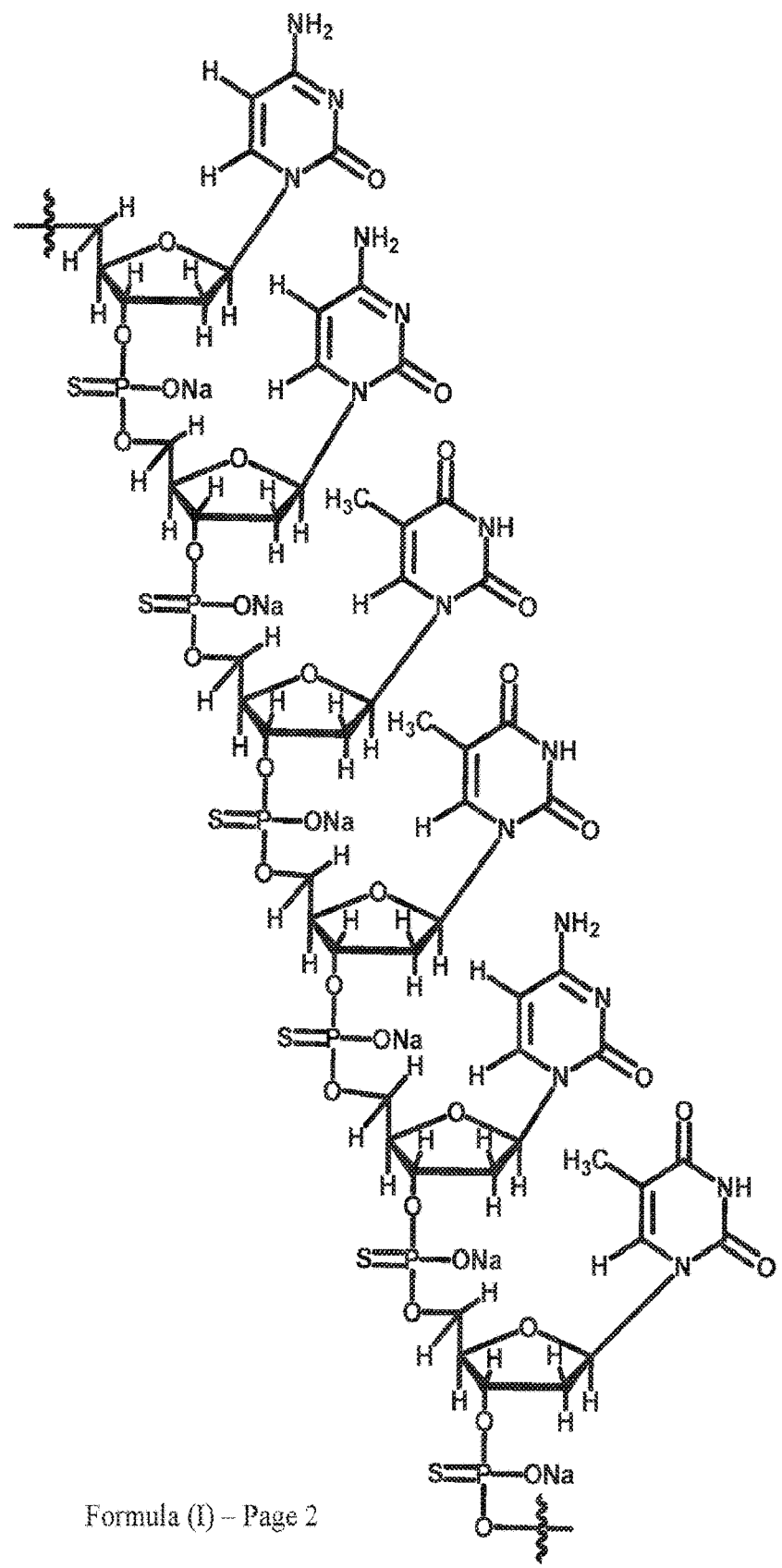
Figure 9C:
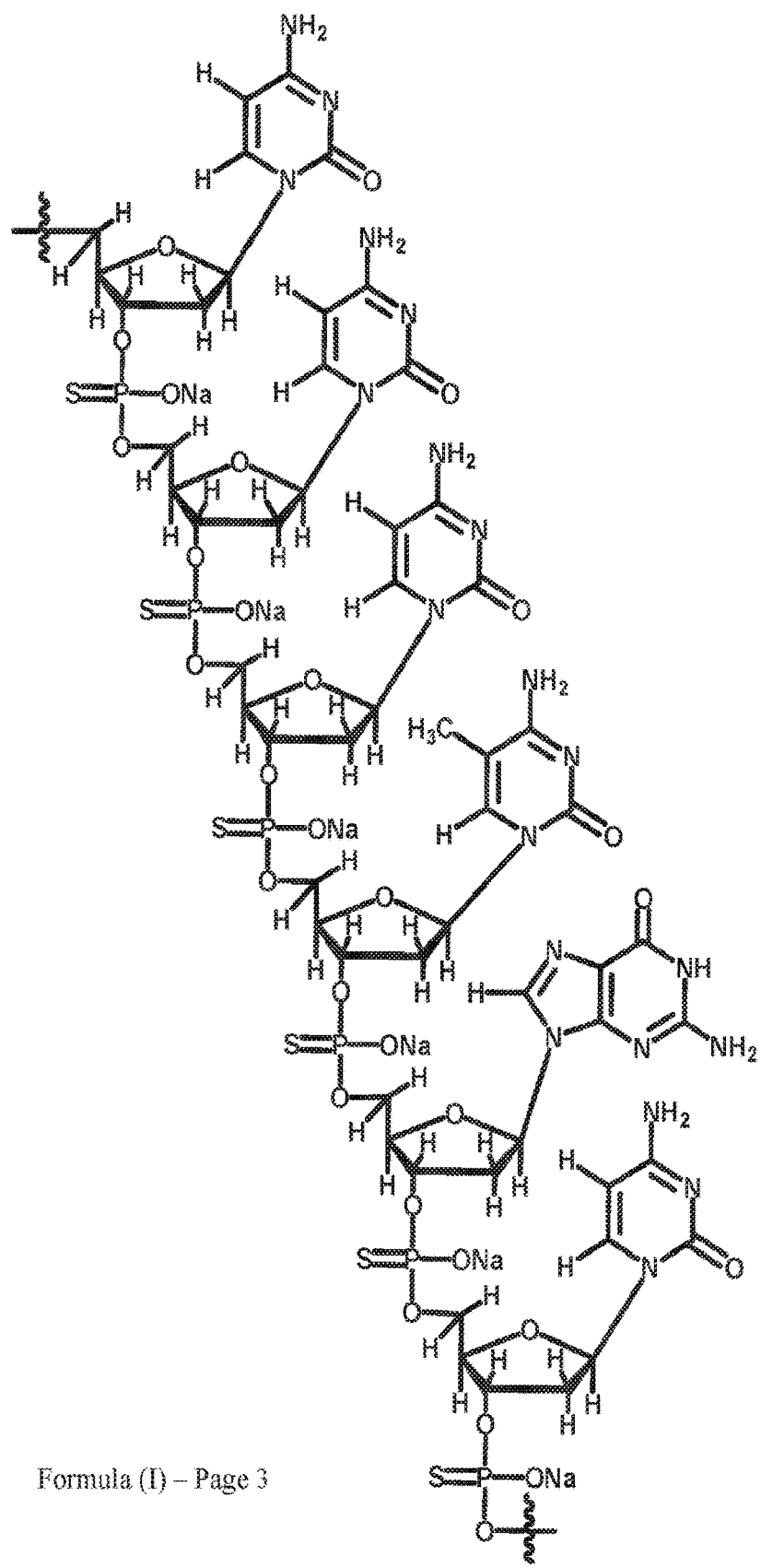
Figure 9D:
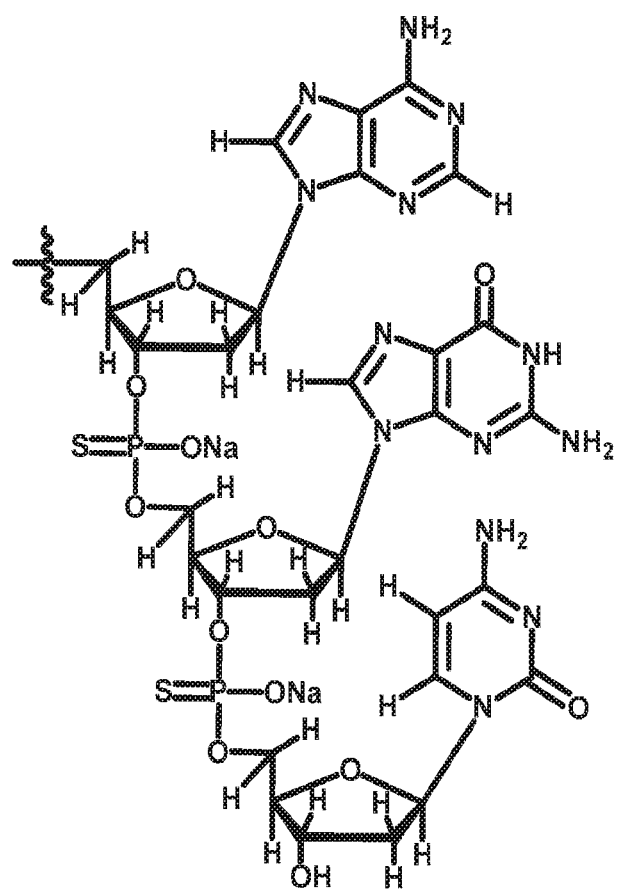

A study was conducted to determine the role of Smad7 in chronic colitis and the development of intestinal fibrosis. Intestinal fibrosis and chronic colitis were induced in Balb/c mice by administration of trinitrobenzene sulfonic acid (TNBS) (FIG. 3). The study consisted of 4 test groups of mice: Group 1: H2O ad libitum; Group 2: TNBS in 35% EtOh; Group 3: TNBS in 35% EtOh+SMAD7 Sense oligonucleotide; and Group 4: TNBS in 35% EtOH+SMAD7 Antisense Oligonucleotide (Mongersen; FIG. 8).

Figure 4:
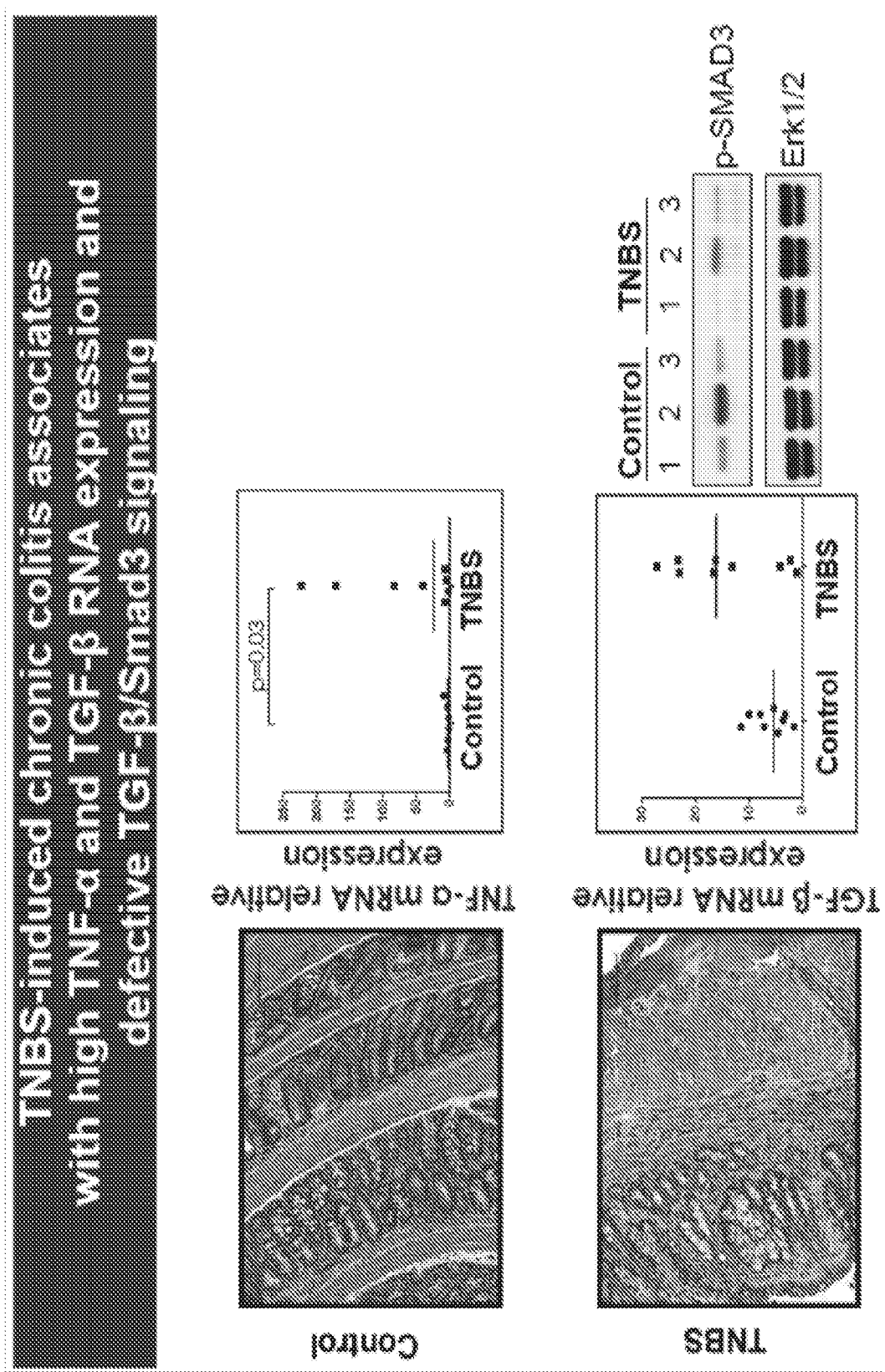
FIG. 4. TNBS induced chronic colitis is associated with high TNF-α and TGF-β RNA expression and defective TGF-β/Smad3 signaling.
Figure 5:
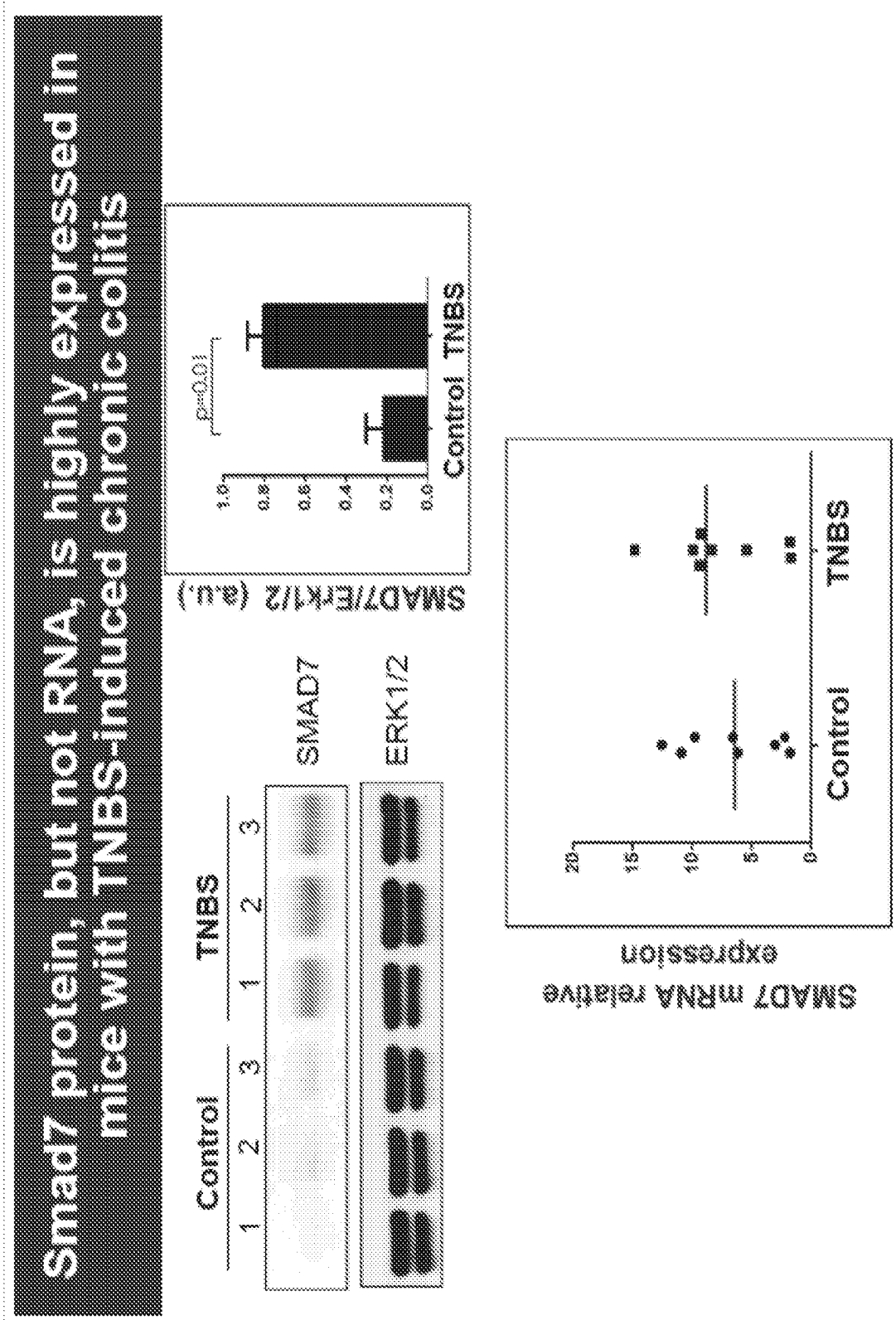
FIG. 5. Smad7 protein, but not RNA, is highly expressed in mice with TNBS-induced chronic colitis.
Figure 6:
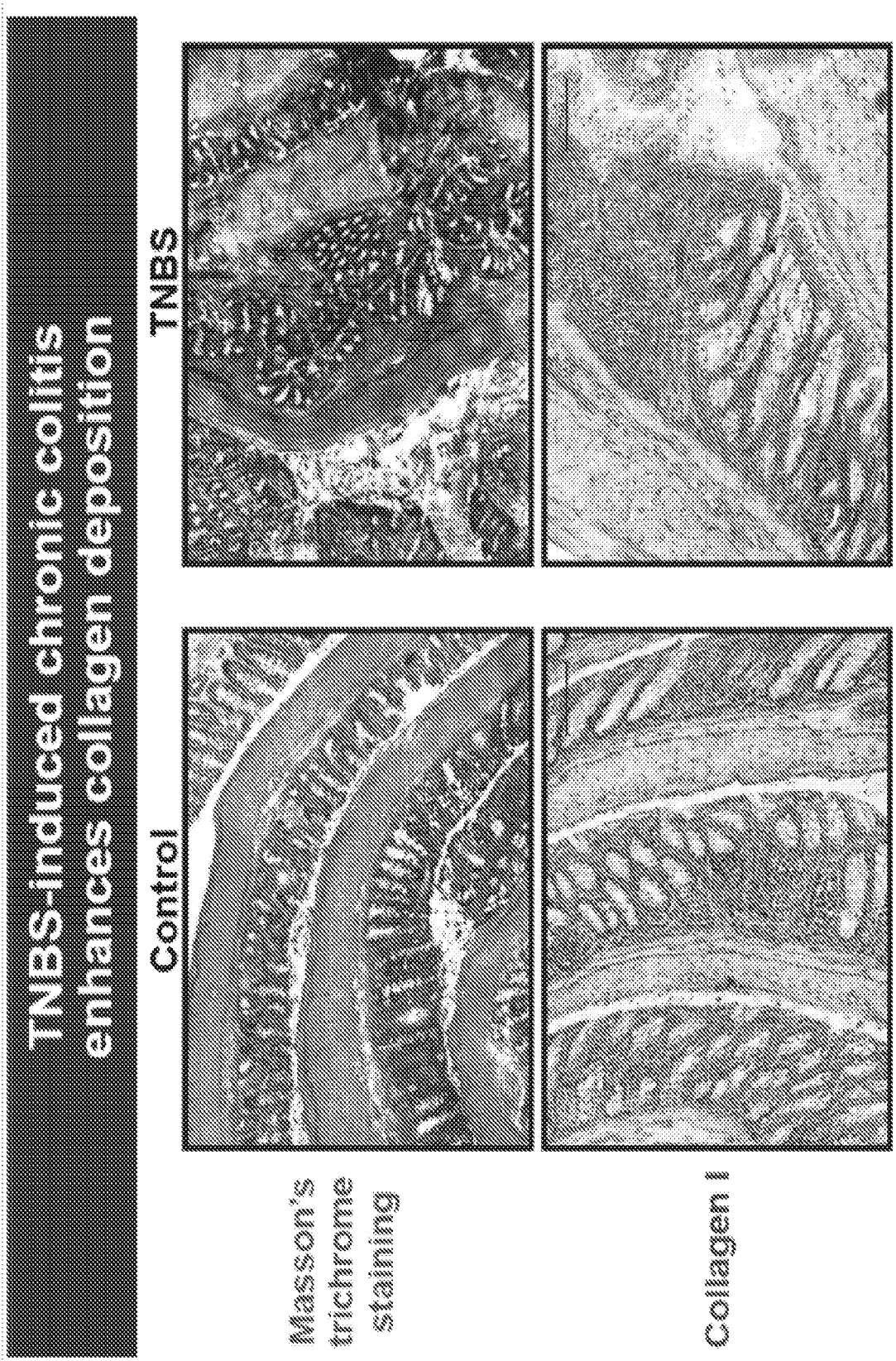
FIG. 6. TNBS-induced chronic colitis enhances collagen deposition.
Figure 7:
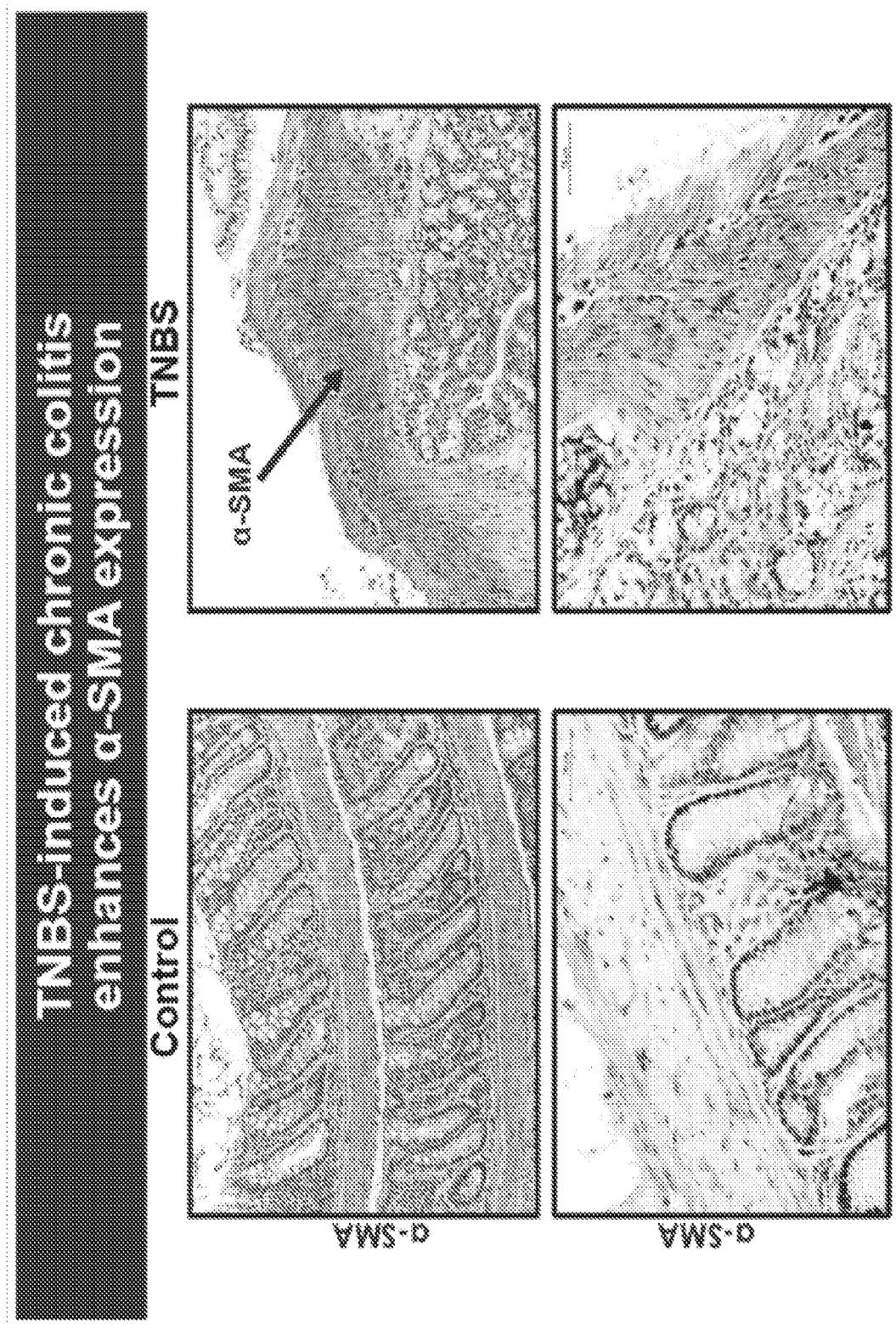
FIG. 7. TNBS-induced chronic colitis enhances α-SMA expression.

A number of observations were made in the TNBS treated mice. First, TNBS treated mice were found to express high levels of TNF-α and TGF-β RNA and were found to be defective in TGF-β/Smad3 signaling (FIG. 4). Second, Smad7 protein, but not RNA, was found to be highly expressed in the mice having TNBS-induced chronic colitis (FIG. 5). Enhanced collagen deposition (FIG. 6) as well as enhanced α-SMA expression (FIG. 7) were also observed in the TNBS-treated mice.

Figure 10:
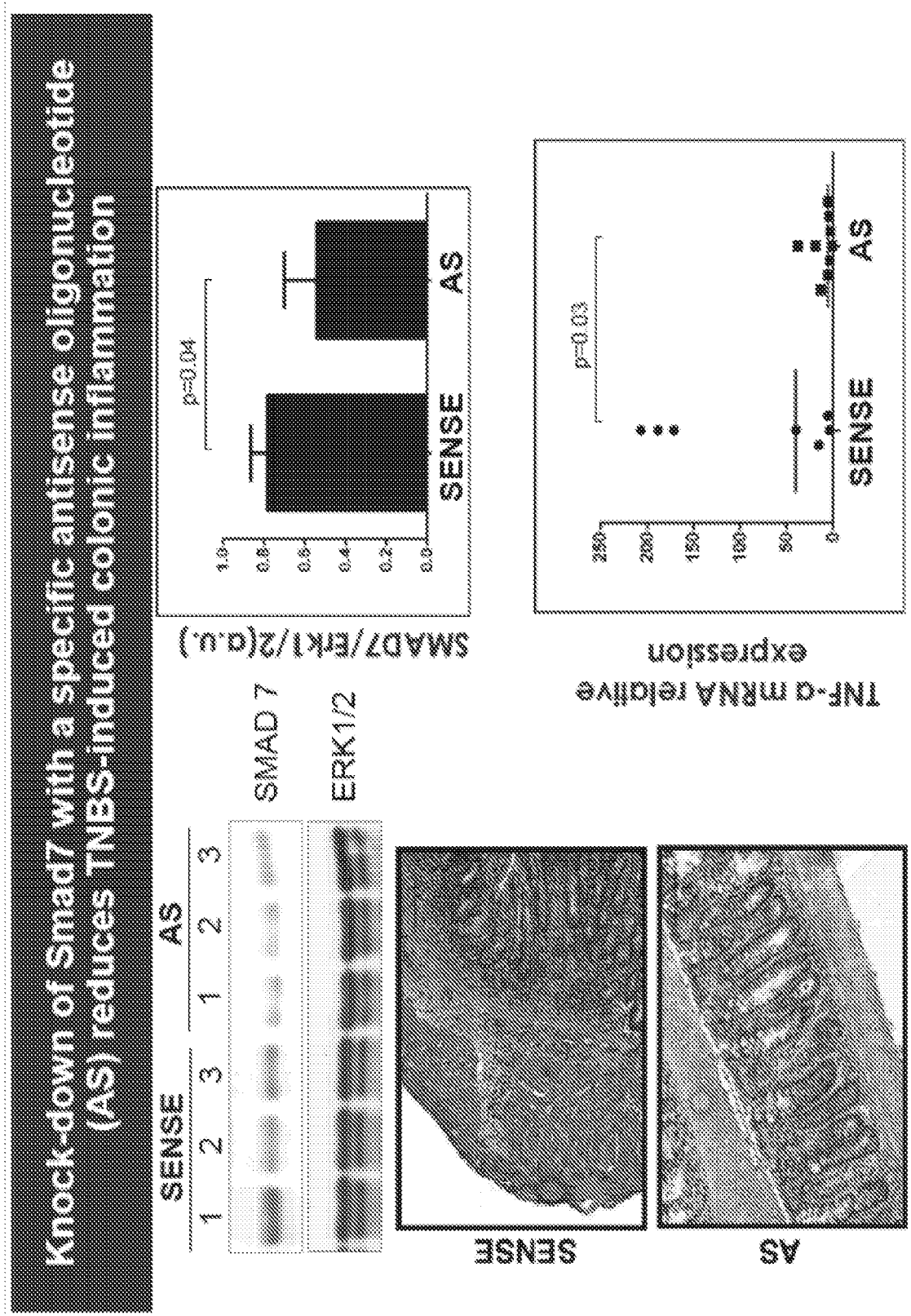
FIG. 10. Knock-down of Smad7 with a specific antisense oligonucleotide (AS) reduces TNBS-induced colonic inflammation.
Figure 11:
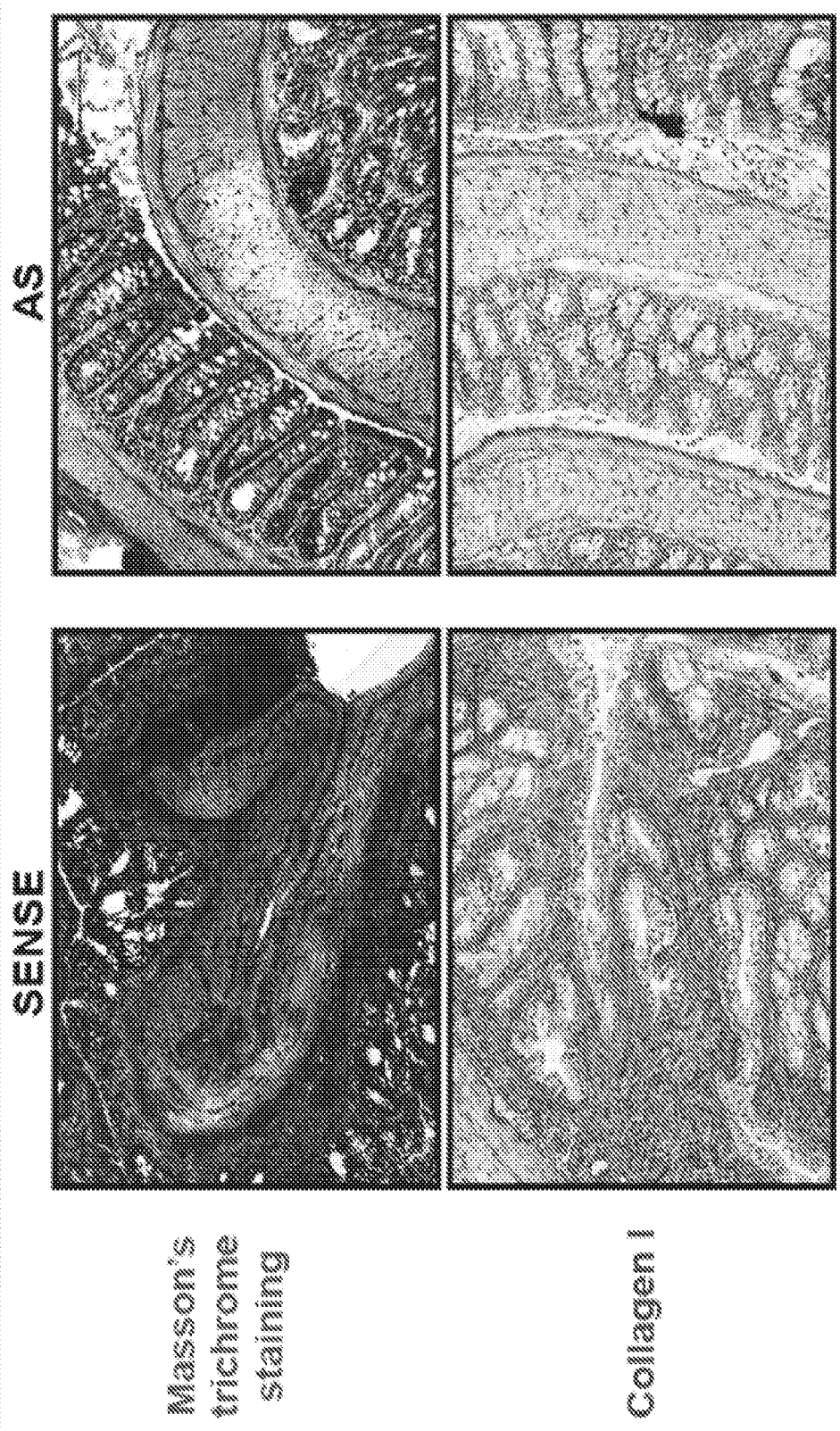
FIG. 11. Treatment of colitic mice with Smad7 antisense oligonucleotide (AS) reduces collagen deposition.
Figure 12:
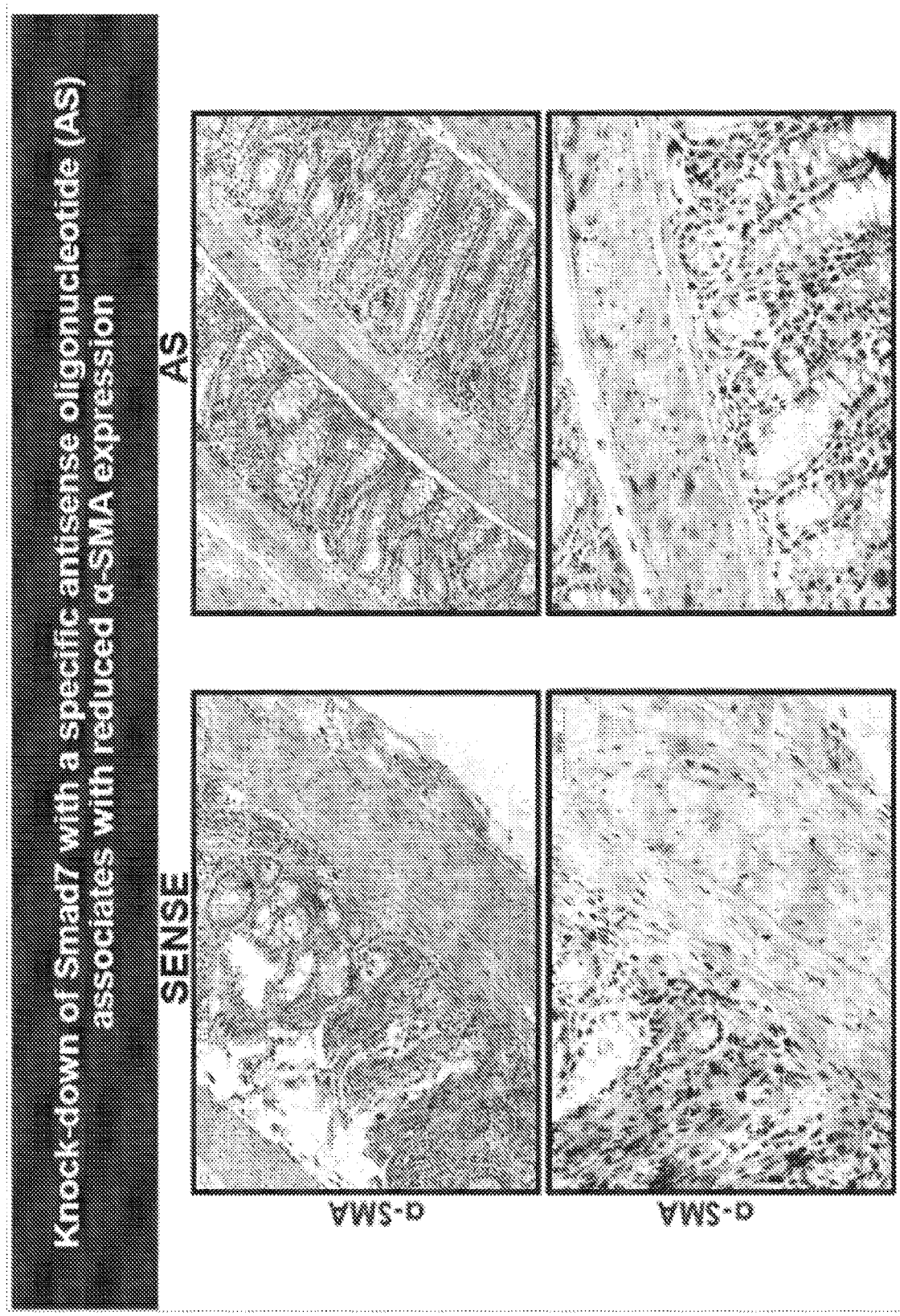
FIG. 12. Knock-down of Smad7 with a specific antisense oligonucleotide (AS) associates with reduced α-SMA expression.
Figure 13:
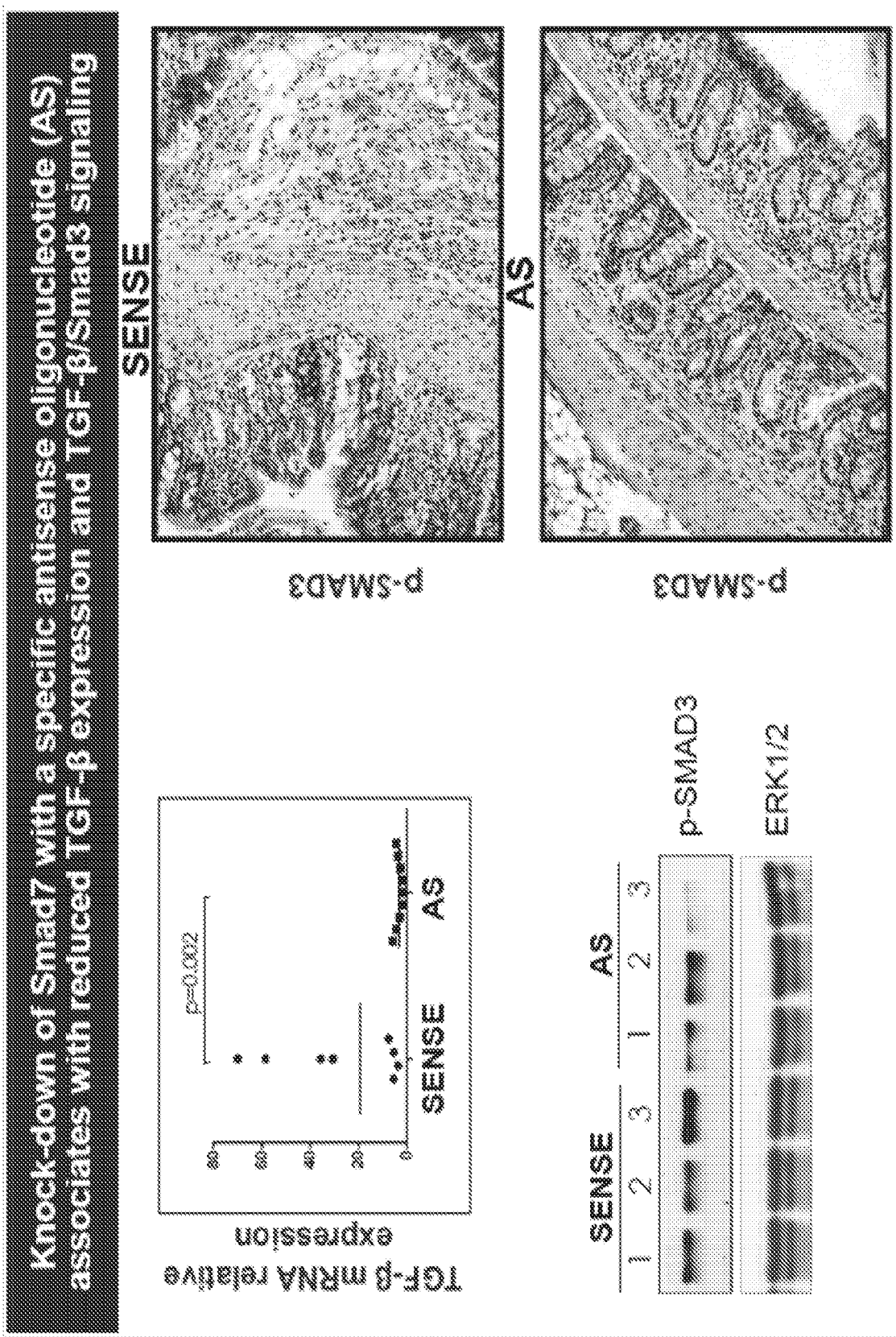
FIG. 13. Knock-down of Smad7 with a specific antisense oligonucleotide (AS) associates with reduced TGF-β expression and TGF-β/Smad3 signaling.

Following treatment with TNBS, the mice were exposed to either a Smad7 sense oligonucleotide or a Smad7 antisense oligonucleotide. Administration of the Smad7 antisense oligonucleotide (FIG. 9), resulted in a knock-down of Smad7 expression and a reduction in TNBS-induced colonic inflammation (FIG. 10) and collagen deposition (FIG. 11). The knock-down in Smad-7 expression was also found to be associated with reduced α-SMA expression (FIG. 12), TGF-β expression and TGF-β/Smad3 signaling (FIG. 13).

These results confirm that knockdown of Smad7 with antisense oligonucleotides ameliorates chronic colitis and limits the development of intestinal fibrosis.

INCORPORATION BY REFERENCE

The entire disclosure of each of the patent documents and scientific articles cited herein is incorporated by reference for all purposes.

EQUIVALENTS

The invention can be embodied in other specific forms with departing from the essential characteristics thereof. The foregoing embodiments therefore are to be considered illustrative rather than limiting on the invention described herein. The scope of the invention is indicated by the appended claims rather than by the foregoing description, and all changes that come within the meaning and range of equivalency of the claims are intended to be embraced therein.

What is claimed is:

1. A method for ameliorating inflammatory bowel disease or limiting the development of intestinal fibrosis in a patient in need thereof, wherein the method comprises determining and analyzing the level of TGF-β (Transforming Growth Factor-β), p-SMAD3 (phosphorylated SMAD3), and/or α-SMA (α-Smooth Muscle Actin) in the patient thereby determining or adjusting the dose of a SMAD7 antisense oligonucleotide, wherein the method comprises
  (a) administering to the patient an initial dose of a SMAD7 antisense oligonucleotide;
  (b) analyzing the level of TGF-β, p-SMAD3, and/or α-SMA in the patient; and
  (c) (i) if the level of TGF-β is above normal levels of TGF-β, then administering to the patient a subsequent dose that is greater than or equal to the initial dose, or, if the level of TGF-β is below normal levels of TGF-β, then administering to the patient a subsequent dose that is equal to or smaller than the initial dose;
  (ii) if the level of p-SMAD3 is above normal levels of p-SMAD3, then administering to the patient a subsequent dose that is greater than or equal to the initial dose, or, if the level of pSMAD3 is below normal levels of p-SMAD3, then administering to the patient a subsequent dose that is equal to or smaller than the initial dose; and/or
  (iii) if the level of α-SMA is lower than the control level, then administering to the patient a subsequent dose that is the same as the initial dose or smaller than the initial dose, or, if the level of α-SMA is unchanged or increased compared to the control level, then administering to the patient a subsequent dose that is the same as the initial dose or greater than the initial dose or terminating the treatment, wherein the control level of α-SMA for the patient is established prior to administering to the patient an initial dose of a SMAD7 antisense oligonucleotide.

2. The method of claim 1, wherein the method comprises determining and analyzing the level of TGF-β in the patient.

3. The method of claim 1, wherein the method comprises determining and analyzing the level of pSMAD3 in the patient.

4. The method of claim 1, wherein the method comprises determining and analyzing the level of a α-SMA in the patient.

5. The method of claim 1, wherein the SMAD7 antisense oligonucleotide comprises an oligonucleotide selected from the group consisting of SEQ ID NO: 2, SEQ ID NO: 3, and SEQ ID NO: 4.

6. The method of claim 1, wherein the inflammatory bowel disease is Crohn's disease or colitis.

7. The method of claim 6, wherein the colitis is acute or chronic.

8. The method of claim 1, wherein the SMAD7 antisense oligonucleotide is comprised in a pharmaceutical composition comprising an enteric coating comprising an ethylacrylate-methacrylic acid copolymer.

9. The method of claim 1, wherein the SMAD7 antisense oligonucleotide is administered parenterally or orally.

10. The method of claim 1, wherein the initial dose of the SMAD7 antisense oligonucleotide is at least 100 µg.

11. The method of claim 1, wherein the initial dose of the SMAD7 antisense oligonucleotide from 35 mg to 500 mg.

12. The method of claim 1, wherein the patient is a human.

* * * * *

SEQUENCE LISTING

```
<160> NUMBER OF SEQ ID NOS: 5

<210> SEQ ID NO 1
<211> LENGTH: 1281
<212> TYPE: DNA
<213> ORGANISM: Homo sapiens
<220> FEATURE:
<223> OTHER INFORMATION: human SMAD7 mRNA (sequence based on CDS of
      NM_005904.3)

<400> SEQUENCE: 1
atgttcagga ccaaacgatc tgcgctcgtc cggcgtctct ggaggagccg tgcgcccggc        60
ggcgaggacg aggaggaggg cgcaggggga ggtggaggag gaggcgagct gcggggagaa       120
ggggcgacgg acagccgagc gcatggggcc ggtggcggcg gcccgggcag ggctggatgc       180
tgcctgggca aggcggtgcg aggtgccaaa ggtcaccacc atccccaccc gccagccgcg       240
ggcgccggcg cggccggggg cgccgaggcg gatctgaagg cgctcacgca ctcggtgctc       300
aagaaactga aggagcggca gctggagctg ctgctccagg ccgtggagtc ccgcggcggg       360
acgcgcaccg cgtgcctcct gctgcccggc cgcctggact gcaggctggg cccggggcg       420 cccgccggcg cgcagcctgc gcagccgccc tcgtcctact cgctcccct cctgctgtgc       480
```

```
aaagtgttca ggtggccgga tctcaggcat tcctcggaag tcaagaggct gtgttgctgt    540
gaatcttacg ggaagatcaa ccccgagctg gtgtgctgca accccatca ccttagccga    600 ctctgcgaac tagagtctcc ccccctcct tactccagat acccgatgga ttttctcaaa    660
ccaactgcag actgtccaga tgctgtgcct tcctccgctg aaacaggggg aacgaattat    720
ctggcccctg gggggctttc agattcccaa cttcttctgg agcctgggga tcggtcacac    780
tggtgcgtgg tggcatactg ggaggagaag acgagagtgg ggaggctcta ctgtgtccag    840
gagccctctc tggatatctt ctatgatcta cctcagggga atggcttttg cctcggacag    900
ctcaattcgg acaacaagag tcagctggtg cagaaggtgc ggagcaaaat cggctgcggc    960
atccagctga cgcgggaggt ggatggtgtg tgggtgtaca accgcagcag ttaccccatc   1020
ttcatcaagt ccgccacact ggacaacccg gactccagga cgctgttggt acacaaggtg   1080
ttccccggtt tctccatcaa ggctttcgac tacgagaagg cgtacagcct gcagcggccc   1140
aatgaccacg agtttatgca gcagccgtgg acgggcttta ccgtgcagat cagctttgtg   1200
aagggctggg gccagtgcta cacccgccag ttcatcagca gctgcccgtg ctggctagag   1260
gtcatcttca acagccggta g                                             1281
```

<210> SEQ ID NO 2
<211> LENGTH: 21
<212> TYPE: DNA
<213> ORGANISM: Artificial Sequence
<220> FEATURE:
<223> OTHER INFORMATION: antisense oligonucleotide of SMAD7

<400> SEQUENCE: 2

```
gtcgcccctt ctccccgcag c                                               21
```

<210> SEQ ID NO 3
<211> LENGTH: 20
<212> TYPE: DNA
<213> ORGANISM: Artificial Sequence
<220> FEATURE:
<223> OTHER INFORMATION: antisense oligonucleotide of SMAD7
<220> FEATURE:
<221> NAME/KEY: misc_feature
<222> LOCATION: (3)..(3)
<223> OTHER INFORMATION: n is a nucleotide comprising 5-methyl-2'-
      deoxycytidine and wherein the internucleotide linkages are
      phosphorothioate linkages
<220> FEATURE:
<221> NAME/KEY: misc_feature
<222> LOCATION: (16)..(16)
<223> OTHER INFORMATION: n is a nucleotide comprising 5-methyl-2'-
      deoxycytidine and wherein the internucleotide linkages are
      phosphorothioate linkages

<400> SEQUENCE: 3

```
gtngcccctt ctcccngcag                                                 20
```

<210> SEQ ID NO 4
<211> LENGTH: 21
<212> TYPE: DNA
<213> ORGANISM: Artificial Sequence
<220> FEATURE:
<223> OTHER INFORMATION: antisense oligonucleotide of SMAD7
<220> FEATURE:
<221> NAME/KEY: misc_feature
<222> LOCATION: (3)..(3)
<223> OTHER INFORMATION: n is 5-methyl-2'-deoxycytidine and
      wherein the internucleotide linkages are phosphorothioate linkages
<220> FEATURE:
<221> NAME/KEY: misc_feature

```
<222> LOCATION: (16)..(16)
<223> OTHER INFORMATION: n is 5-methyl-2'-deoxycytidine and
      wherein the internucleotide linkages are phosphorothioate linkages

<400> SEQUENCE: 4
gtngcccctt ctcccngcag c                                              21

<210> SEQ ID NO 5
<211> LENGTH: 20
<212> TYPE: DNA
<213> ORGANISM: Artificial Sequence
<220> FEATURE:
<223> OTHER INFORMATION: antisense oligonucleotide of SMAD7
<220> FEATURE:
<221> NAME/KEY: misc_feature
<222> LOCATION: (3)..(3)
<223> OTHER INFORMATION: n is a nucleotide comprising a nitrogenous base
      selected from the group consisting of cytosine and
      5-methylcytosine or a 2'-O-methylcytosine nucleoside
<220> FEATURE:
<221> NAME/KEY: misc_feature
<222> LOCATION: (4)..(4)
<223> OTHER INFORMATION: n is a nucleotide comprising a nitrogenous base
      selected from the group consisting of guanine and 5-methylguanine
      or a 2'-O-methylguanine nucleoside
<220> FEATURE:
<221> NAME/KEY: misc_feature
<222> LOCATION: (16)..(16)
<223> OTHER INFORMATION: n is a nucleotide comprising a nitrogenous base
      selected from the group consisting of cytosine and
      5-methylcytosine or a 2'-O-methylcytosine nucleoside
<220> FEATURE:
<221> NAME/KEY: misc_feature
<222> LOCATION: (17)..(17)
<223> OTHER INFORMATION: n is a nucleotide comprising a nitrogenous base
      selected from the group consisting of guanine and 5-methylguanine
      or a 2'-O-methylguanine nucleoside

<400> SEQUENCE: 5
gtnncccctt ctcccnncag                                                20
```